United States Patent
Bidwell et al.

(12)

(10) Patent No.: US 6,277,592 B1
(45) Date of Patent: Aug. 21, 2001

(54) PORCINE LEPTIN PROTEIN, NUCLEIC ACID SEQUENCES CODING THEREFOR AND USES THEREOF

(75) Inventors: Christopher A. Bidwell, West Lafayette, IN (US); Michael E. Spurlock, Pacific, MO (US)

(73) Assignees: Purina Mills, Inc., St. Louis, MO (US); Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 08/692,922

(22) Filed: Jul. 31, 1996

(51) Int. Cl.[7] .................... C07K 14/435; C12N 15/12; C12N 15/63; C12N 1/21
(52) U.S. Cl. ............... 435/69.1; 435/252.3; 435/320.1; 435/325; 530/350; 536/23.5
(58) Field of Search .................. 536/23.5; 435/69.1, 435/252.3, 320.1, 325; 530/350

(56) References Cited

U.S. PATENT DOCUMENTS

| | | |
|---|---|---|
| 3,507,662 | 4/1970 | Leroy et al. . |
| 3,619,200 | 11/1971 | Ferguson et al. . |
| 3,695,891 | 10/1972 | Fox . |
| 4,237,224 | 12/1980 | Cohen et al. . |
| 4,358,535 | 11/1982 | Falkow et al. . |
| 4,376,110 | 3/1983 | David et al. . |
| 4,377,576 | 3/1983 | Schmidt et al. . |
| 4,446,237 | 5/1984 | Berninger . |
| 4,563,417 | 1/1986 | Albarella et al. . |
| 4,581,333 | 4/1986 | Kourilsky et al. . |
| 4,582,788 | 4/1986 | Erlich . |
| 4,582,789 | 4/1986 | Sheldon, III et al. . |
| 4,683,194 | 7/1987 | Saiki et al. . |
| 4,683,202 | 7/1987 | Mullis . |
| 5,089,397 | 2/1992 | Kushner et al. . |
| 5,268,295 | 12/1993 | Serrero . |
| 5,362,629 | 11/1994 | Schreiber et al. . |
| 5,935,810 | * 8/1999 | Friedman et al. . |
| 6,001,968 | * 12/1999 | Friedman et al. . |

FOREIGN PATENT DOCUMENTS

| | | |
|---|---|---|
| 050424 | 4/1982 | (EP) . |
| 084796 | 8/1983 | (EP) . |
| 119448 | 9/1984 | (EP) . |
| 144914 | 6/1985 | (EP) . |
| 201184 | 12/1986 | (EP) . |
| 237362 | 9/1987 | (EP) . |
| 258017 | 3/1988 | (EP) . |
| 0743321 | * 11/1996 | (EP) . |
| 2 292 382 | 2/1996 | (GB) . |
| WO 93/03050 | 2/1993 | (WO) . |
| WO 93/16183 | 8/1993 | (WO) . |
| 9605309 | * 2/1996 | (WO) . |
| WO 97/02004 | 1/1997 | (WO) . |

OTHER PUBLICATIONS

Sasaki et al, *Mammalian Genome* 7, 1996 (Jun.) p471.*
Frederich et al, *J. Clin Invest* 96, 1995 (Sep.), p 1658–63.*
Murakami et al, *B.B.R.C.* 209(3) 1995, p. 944–52.*
He et al, *JBC* 270(48) 1995, p. 28887–91.*
Green et al, *Genome Research* 5. 1995, p. 5–12.*
Altmann et al Protein Expression & Purification 6, 1995, p. 722–26.*
Ogawa et al, *J Clin Invest* 96, 1995, p 1647–52.*
Masuzaki et al. *Diabetes* 44, 1995, p. 855–58.*
Neuenschwander et al, *Animal Genetics* 27, 1996, p 275–78.*
Andersson et al, *Annals Medicine* 28, 1996, p 5–7.*
Hausmon et al, *FASEB Journal* 10(3) Mar. 1996, p A186.*
Yen et al, *FASEB Journal* 11(3) Feb. 1997, p A415.*
Ramsay et al *FASEB Journal* 11(3) Feb. 1997, p A416.*
Archibald et al, *Mammalian Genome* 6, 1995, p157–175.*
Funohashi et al, *BBRC* 211(2) 1995, p 469–75.*
Leroy, Pascale, et al., "Expression of Ob Gene in Adipose Cells", *The Journal of Biological Chemistry*, vol. 271, No. 5, Issue of Feb. 2, pp. 2365–2368, 1996.
Saladin, Regis, et al., "Transient Increase in Obese Gene Expression After Food Intake or Insulin Administration", *Nature*, vol. 377, pp. 527–529, Oct. 12, 1995.
Campfield, L. Arthur, et al., "Recombinant Mouse Ob Protein: Evidence For a Peripheral Signal Linking Adiposity and Central Neural Networks", *Science*, vol. 269, pp. 546–549, Jul. 28, 1995.
Halaas, Jeffery L., et al., "Weight–reducing Affects of the Plasma Protein Encoded by the Obese Gene", *Science*, vol. 269, pp. 543–546, Jul. 28, 1995.

(List continued on next page.)

Primary Examiner—Christine J. Saoud
(74) Attorney, Agent, or Firm—Whyte Hirschboeck Dudek SC

(57) ABSTRACT

A porcine adipocyte-specific polypeptide, termed leptin, is expressed in the fat tissue of pigs. Expression may be altered in over fat pigs, or expression may be in the form of a protein of lesser biological activity relative to that of leaner pigs. The porcine adipocyte polypeptide, DNA and RNA molecules coding therefor, methods for its preparation, and antibodies specific for the polypeptide are disclosed. Methods for determining the susceptibility of a pig to fat deposition are based on measuring the levels of the porcine adipocyte polypeptide in a biological fluid or tissue extract or by measuring mRNA encoding the porcine adipocyte polypeptide in cells of the subject. Methods of evaluating an agent related to the deposition of fat in swine comprise contacting the agent with an adipocyte in vitro and measuring the amount of the porcine adipocyte polypeptide or mRNA that is produced by the adipocyte. Methods of limiting fat deposition include administering porcine leptin or porcine leptin DNA, and methods of regulating intake include administering porcine leptin, porcine leptin DNA, or an antibody directed against porcine leptin.

12 Claims, 10 Drawing Sheets

OTHER PUBLICATIONS

Pelleymounter, Mary Ann, et al., "Effects of the Obese Gene Product on Body Weight Regulation in Ob/Ob Mice", *Science*, vol. 269, pp. 540–543, Jul. 28, 1995.

Maffei, Margherita, et al., "Increased Expression in Adipocytes of Ob RNA in Mice with Lesions of the Hypothalamus and with Mutations at the DB Locus", *Proc. Natl. Acad. Sci. USA*, vol. 92, pp. 6957–6960, Jul. 1995.

Zhang, Yiying, et al., "Positional Cloning of the Mouse Obese Gene and its Human Homologue", *Nature*, vol. 372, pp. 425–432, Dec. 1, 1994.

Better, Marc, et al., "*Escherichia coli* Secretion of an Active Chimeric Antibody Fragment", *Science*, vol. 240, May 20, 1988.

Liu, Alvin Y. et al., "Chimeric Mouse–human IgG1 Antibody that can Mediate Lysis of Cancer Cells", *Proc. Natl. Acad. Sci. USA*, vol. 84, pp. 3439–3443, May 1987.

Chomczynski, Piotr, & Sacchi, Nicoletta, "Single–step Method of RNA Isolation by Acid Guanidinium Thiocyanate–Phenol–Chloroform Extraction", *Analytical Biochemistry*, 162, 156–159 (1987).

Boulianne, Gabrielle L., et al., "Production of Functional Chimaeric Mouse/Human Antibody", *Nature*, vol. 312, Dec. 13, 1984.

Morrison, Sherie L., et al., "Chimeric Human Antibody Molecules: Mouse Antigen–binding Domains with Human Constant Region Domains", *Proc. Natl. Acad. Sci. USA*, vol. 81, pp. 6851–6855, Nov. 1984.

Cabilly, Shmuel, et al., "Genration of Antibody Activity From Immunoglobulin Polypeptide Chains Produced in *Escherichia coli*", *Proc. Natl. Acad. Sci. USA*, vol. 81, pp. 3273–3277, Jun. 1984.

Wahl, Richard L., "Improved Radioimaging and Tumor Localization with Monoclonal F(ab')2", *J. Nucl. Med.* 24:316–325, 1983.

De St. Groth, S. Fazekas, & Scheidegger, Doris, "Production of Monoclonal Antibodies: Strategy and Tactics", *Journal of Immunological Methods*, 35 (1980) 1–21.

Kohler, G. & Milstein, C., "Continuous Cultures of Fused Cells Secreting Antibody of Predefined Specificity", *Nature*, vol. 256, pp. 495–497 Aug. 7, 1975.

Chen, et al., "Ob Gene Expression During Porcine Preadipocyte Differentiation in Vitro", *Depts. Of Foods and Nutrition and of Animal and Dairy Science*, vol. 10, No. 3, abstract 1075, p. A186, Mar. 8, 1996.

Yen, X., et al., "Porcine Leptin Sequence and Expression in Lean and Obese Pigs", *Depts. Of Foods and Nutrition and of Animal and Dairy Science*, vol. 11, No. 3, abstract 2406, p. A415, Feb. 28, 1997.

* cited by examiner

FIG. 1A

```
   1  AAGCTTTCTTGGCCCCTAACAGCAACCACATTATACTCTTACTGGCTATTCCTTGGCCTT    60
  61  CAATACCCAGCCCAGGGGACCCCTCTTCCAGGGAGCCCCGCTTGTACTCCTGAGATGTCA   120
 121  TGTCCTTCTTGCAGAGCTCTTCCTCACGGCATCGGGACGGCGGTTCACCCTTTTGCCTCT   180
 181  CCGGATAAACTGTAAGCTACTTGAGAGCAGAGAACATCCATTGTTCGCTGTGGCATCCGT   240
 241  GGTACCTAGCACGGCATCTGACATATTATCAGATCTTCCACAAAGGCCAGTTTACGGTTG   300
 301  AATGCCCGTTGAATTCAGGCTCCCAGTGGGAGAGCGAGGAAGTAATAAAGCCGGTGATAA   360
 361  ATGCCGCCGTGGAGACACCAGCGGGCTGCCGTGAGACTAATGGAGAGGACAGTAACGTTA   420
 421  TCTCTAATGCGAGGGTGGTTATAGAGTACATTTCATAACACCTTTAAAGCTCTTTCACAC   480
 481  GCATTATCCAATTTGATCCTCATAAAAGCCTGGAGATGTGTATATTGTGGTGGATGGAGG   540
 541  GGGAGTCTTTAGCAGTTATGGGATATGCCTGAAGTCGTGCAGCTAGTAAATGGCTGGATT   600
 601  CAAACCAGACCTCAAAAGCCTGCCTGTTTGCTCATGCCCCCTGCCCCGACTGCCCACTCT   660
 661  GTGGCCCACAGCACAACTCACCGTCGCTTTCTTGATCCGTTTTCTTGATCCGGCTGTGCT   720
 721  CTCCCCAAGGAATGCTTTTCATTAACATATGTCTAGGTAATGAATTATCTTGACTCTGAG   780
 781  GAGGCCATAGCACATGCCGTAACGCGACAGCTCCTTTGATCTGCATCTGAGGCTGTGGCT   840
 841  GGTAACGGGCGTGGGGAGGGGGCGTTCGCTGAGACCCCAGGGACACGCCATGTGTGGTTC   900
 901  CCTCTGTTTCCAGGCCCCAGAAGCACATCCCGGAAAGGAAAATGCGCTGTGGACCCCTGT   960
                                                M  R  C  G  P  L  C
 961  GCCGATTCCTGCTGGCTTTGGCCTATCTGTCCTACGTTGAAGCCGTGCCCATCTGGAGAG  1020
      R  F  L  L  A  L  A  Y  L  S  Y  V  E  A  V  P  I  W  R  V
1021  TCCAGGATGACACCAAAACCCTCATCAAGACGATTGTCACCAGGATCAGTGACATTTCAC  1080
      Q  D  D  T  K  T  L  I  K  T  I  V  T  R  I  S  D  I  S  H
1081  ACATGGTAGGGAAGGCCTGGGAGACAAGGTCGAACCTGTGGCCAGCCCGGGGGAGGAGG   1140
      M
1141  GGTACCGGACCTCAGAGGTTGGCGGAGGTGGGAAGGGTCGGCGGTGGCCTTGACGCCTCC  1200
1201  CCCACCCCCCCCAACCAGCTGCCTTTGCTCCTCCGCTTCCCTCACCGCACCCCCCCACGT  1260
1261  CCTTATCCTCCTTCTTCCCAGACTGGAATCCTGATGCCCAGGACTAGAGGAAGCCCTAAA  1320
1321  GGTCCTGTGTGCCTTTGCCAGGTGCGCAGACCCCCCAGCATCATCCCCTCTGGCCTCCAT  1380
1381  CACGTCTCCGGAATGTTCTAATCTGTAGGAATTCTTCCTGGTGACAGCTGAACTCTGACC  1440
1441  CTGCGGACGCCCCTTACTGCTAGTCCTGCCCATTGAGCCTTTTTTCCTATACAACCCTCT  1500
1501  ACATGTTTGCAAACTTCTCTCAATGTCCCCAGGGTGTTTTCTCTGGGGTCCGCAGGCCGA  1560
1561  GACCTTCAGCCTCTTCTCAGCTGAGGTCCGTCTTTAGAATTCAGAAGACGAGGTGTGACT  1620
1621  CCTCACCCTGCTGTTCCCTCTCTGTAAAATCTCAAGCACGTTAAGTCCCTCCGTGTCTGA  1680
1681  AACCTTAGTTTCCCTCATCCAGATAATGGGACTGTTACTGGGAAGATGTTACCGGAATCC  1740
1741  AGGGTCTTGCCTCATGGAGCTCAAGAATGAACTTGGCGAACGCACAGGGAGCCGAGCAAG  1800
```

FIG. 1B

```
1801  CAGAAGTCTTTATTACAGGAAGGCAGACAGCTCCCAGCACAGACACGGGGAGGGAAGAGT  1860
1861  CCCCCCGCCCATTGTTCTACGGAGGTTTTTATCACTTAAAGACGGGAGTACCAATGTGGG  1920
1921  GTCCAGATATCCGTTCTTCTTCCCATTGCCCAGTTTACCTATATGGCGCCTTGTCCAGGA  1980
1981  GGGACTCTGTAGAGTTAGGGGTGCTCCGTAAGTTTTATGGTGCGTCTGCTCTTCTCTGCC  2040
2041  CTAGACTTAGAGTCGCCACTCTTTCCATTCTTCTGCTCACAGTCAAATGCATAGGTCAGG  2100
2101  GGTTAATTCCCACCTTCACAGAAATCAAATGTCCTTTCAATAGTTAATCTTCCAATAAGC  2160
2161  AAGGCCTGCTTGTCTTGATTAGTTTTTACAAATCTTAAACCATGGCCATTAATCAGGGAA  2220
2221  GAGATCGAAGCCCATGTTCCCACACTAACTGCCTGAATTATTAGTCTGCCTCAGGACTAT  2280
2281  CTTAATAGTCTTCGCAAGGTTGTTTTGAGATTAAATTAGATAGGAGTTCCTGTCGAGGCG  2340
2341  CGACGGAAACAGATCCGACTCAGAACCATGAGACAGGTTCGATCCCTGGCTTTGTCAGTG  2400
2401  GGTTAGGATCTGGTGCTGCTGTGAGCTGTGGTGTAGGTCGCAGAGGTGGCTCGGATCCCG  2460
2461  CGTTGCTGTGGCTGTGGTGTAGGCCGGTGCAGACAGCTCCGATTAGACCCCTAGCCTGGG  2520
2521  AACCTCCATGTGCCGCGGGTACCGCTAAAAAAAGACAAAAGATGGAAAAAAAAAGGTTA  2580
2581  CATTAGATAAAGCAAGTGACTCCTCCACCACCACACATATCCCTGCAGAACCAGGACAGA  2640
2641  GCATGCCTTCTTGAAAAGTTTTCGGTTGTGGCTTTGATAGCACCCAGCCTTAAAAGCCAG  2700
2701  CTTTTCAATCTGCCCAGAGCAGTCTGGAGACTTCCGCATCTCCTGGCCACTCTGAGTTTC  2760
2761  TAACAGTGGCCTTGGCGAGCCTGGGAGCAGTCCGGTGGCCAGAAGCAGGGACAGCTGAGA  2820
2821  ACCAGATAGAGTCTTGGCACTTTCAAGAGAAAACCCTAAGTCTCCTTCTTCCAGCCATGC  2880
2881  AACAGCTGCGCATGACAGATCCAGCGTGTCCCAGCCTGTGTGGTGCAGGGAGTGAYGCTG  2940
2941  CGNNYAGGGYGYGGGGGAGCTGAGGAGCGAGGCGGGGCATCGNGGGCTGCAGCCTCCAT  3000
3001  CCCTAAGTGGGGAGACTTCATGAAGAGCCTGACCAGNAGGGAGGGGCATGTGTGGAGGAC  3060
3061  CTCAGGGCCTGGGGAAGGCTAGACCCAACTATGTGAGAAACAGACAGTCGTGGCTGGTTC  3120
3121  TACAGAAGAGGCATCTGGAGGCCATTCGAATGCCCAAAGCTGTCTGGGTGAGGCAGGGCT  3180
3181  TGCTAGGCAGAAGACAGAAGGCCGTGAGACCAGCTTGGAGGCTTGGCAGCCACGCCAGCC  3240
3241  CAAGGAGTTCGGGCCTAGATAGGATTGTGTGGAAGGGGAAGAGGCAGCCGGAGGTGGGGG  3300
3301  GTGGGGGTGGACCCGTCTCCACGCCTGCAGGAAGGCCAGGGGCTGCAGAGCCAACATCTC  3360
3361  TCTCGCTGAGCGTCTCGCTCTCCCCTTCCTCCTGCACAGCAGTCTGTCTCCTCCAAACAG  3420
                                                   Q  S  V  S  S  K  Q
3421  AGGGTCACCGGTTTGGACTTCATCCCTGGCTCCATCCTGTCCTGAGTTTGTCCAAGATG  3480
       R  V  T  G  L  D  F  I  P  G  L  H  P  V  L  S  L  S  K  M
3481  GACCAGACCCTGGCGATCTACCAACAGATCCTCACCAGTCTGCCTTCCAGAAATGTGATC  3540
       D  Q  T  L  A  I  Y  Q  Q  I  L  T  S  L  P  S  R  N  V  I
3541  CAAATATCGAATGACCTGGAGAACCTCCGGGACCTTCTCCACCTGCTGGCCTCCTCCAAG  3600
       Q  I  S  N  D  L  E  N  L  R  D  L  L  H  L  L  A  S  S  K
3601  AGCTGCCCCTTGCCCAGCAGGGcCCTGGAGACCTTGGAGAGCCTGGGCGGCGTCCTGGAA  3660
       S  C  P  L  P  S  R  A  L  E  T  L  E  S  L  G  G  V  L  E
```

FIG. 1C

```
3661  GCCTCCCTCTACTCCACGGAGGTGGTGGCCCTGAGCAGGCTGCAGGGGGCTCTGCAGGAC  3720
       A  S  L  Y  S  T  E  V  V  A  L  S  R  L  Q  G  A  L  Q  D
3721  ATGCTGCGGCAGCTGGACCTCAGCCCTGGCTGCTGAAGCTTGAAGGCCTCTCTCCCCAC   3780
       M  L  R  Q  L  D  L  S  P  G  C  *
3781  AGTCGGGGGAAGAAACCTGAGCTTCCAGGAGTCTGCTGGAGAAGAGAGCCTGTGCGGACC  3840
3841  TCCTCTCTGCAGGTCTGCGGACCATTTCTCTCTCGCTCCGCTAAGCTGCTCTTCCAAAGG  3900
3901  CAGAAAACTCCAAGGCACGACACCAAAGACAGAAAGGCCTGGTTCCGCGCCCACCGGAAA  3960
3961  GGGGGCGCCGTCCAGCCAACGGTGGACTAGATTTCGGATTTTCCACCAACGTCTTCCTTC  4020
4021  CTGTTCCATCTCCAGCTCACCGCGTGCTTCAGCGTGACCGGGGGGATTTCAGAGCCTTTC  4080
4081  GACCATCAAGCAGGGTTCCATCTGAGAATTCCGGGGAGCACGGTGAAGGCTACAGGCACA  4140
4141  CACAGCTGGATGCTCCCACGCAACACAAGTTGGAAGCATTTCTTTATTTATTATGCGGTG  4200
4201  TATTCTGGTTGGATTTGAAGCAAAACACCAGCCTTTCCAGGCTCTCTGGGGTCAGCCGGG  4260
4261  GCTAGGGGGAGGCTCCCGAGGTGCTGTTTCCAGTACCATCCATGGGCCTGCTGAGGCCAA  4320
4321  CCCATTTTGAGTGACTTGAGGGCTCTCAAGGTCGTTCTCTAGAGACTGGCTTTGTTTCTA  4380
4381  CTGTGACTGACTTTAAAACTGCAGCGTGTGCACTGGCATCGCCTGCGCGGATCTCGAAGG  4440
4441  GCCAGGTTCTCTTAGAAAGAAGAAGATGAACTTTGTCAGGGGTGTGTACGCGGAGACAGG  4500
4501  AAGTGTGTTGGTGGGCGGGGCATGGATCCAGAATGTGTATTTCTTGTGTGATGGACATTT  4560
4561  GTGTGAGGGGCTCTCTGGACAGGGTGAGGTCATTGTCTCATCTTCGTGGTTTTCATGAGA  4620
4621  GAAGGAGATGATTCCTTCACGGGGGTCGTGGGGTTTTGCCAGCCGCCCGTGCAGGAGTGG  4680
4681  GGAAGGGGCTGAAGCCGAAGACCGTTGGGGGCCGTGGTGAGCTCTGCCTTCTCCAGCTGC  4740
4741  TAGAGGCTGGTCTTTCTCATCAGGGAGTGAGGGTCTCGCGTTGGAGACAGTGATCCCCAG  4800
4801  GGCGGGATCCTTGCCGTGGCCCTCTGAATGGTCTGGGTGATCCCACACTGATGTCATAAC  4860
4861  AGGGAAGTGCCCTGGTTTGGGATTTGTATGCTCACCCAAAGCAAGGGCCTGCTTCCCATC  4920
4921  CATTTTGGGAAGGATTTTTTCTCCAGGGGGAGGGTGAAAGCTCTGGGAGGTCTGTGGGCT  4980
4981  TACGAGATGGTCCAAGTCCTGGGTCAGTGAGTCCCGGGACTCGTGACCGCCTCGAGGAGC  5040
5041  CCCCTTCTCCCTACAGGTCATGTTCAATAGGTCAAACAAGGAGGCATGGGTTTCCACCAT  5100
5101  CCTGCCGCTGTGATGCAGCCATCGCACTACAGGAGGTAGATCTGTCCAAGGAAATTTGAA  5160
5161  TCTCAAGCAATCACTTTCAAGACTGAGCATCTATTGTGCTCAGCCCCAACTGGTGCTATG  5220
5221  GGCTCAGAGAAGCTCATCAAATAAATATTAAAATCCAGTCCTGCCTTCAGGACCTTGCAT  5280
5281  TCCAGATGATAACACCTCCCCCACACCCCGTCTGCAGAGGCTGTCATTTCACCATGGCAA  5340
5341  CCGAGCAGCTGAAACACAGTGCGGTCCTCAGCAGGTGGAAAGGCTGAGCTGAGGAGGGCA  5400
5401  GTGCCCGGGCCCACAGGCTAACCCTGCTTGCACTTGGTAGCATTTTACTGTCGGGGCG    5460
5461  CATCAGCATCTATTACTGAGAAGCCGCATCCCTTTGAAGCAGGATAGCTGAGACTATAAA  5520
5521  AATAAGAAAATACCAGAGTTCCCTTGTGGCACAGAGGGCTAAGGATCCAGTGTTGTTGCT  5580
5581  GCAGCAGCTTGGGTCACGGCTGTGGCAAGGGTTCGATCCCTGGCCTGGGAACTTTCACAT  5640
```

FIG. 1D

```
5641  GTTGCAGGCAAGGCCAAAAAAAAATAAATAAATAAAAATAAACAAAAAAAAACAAGACCA  5700
5701  TAACAGCAGACTGGTGGCAAACCAGGACTAGAACCTGGGTCCTCTGACCCCTAGAGTCAG  5760
5761  TGTCCCCTGAGCCAGCTAGTGTTCTCTGGGGACGGGAACAGGGTTGGGCAGGGAGTTCAG  5820
5821  GAAGTGTTTGCTGGAAGAGCGGAGTTTCCAGGCTGATTTTGCAGGAGGTGAGGGAAGTGG  5880
5881  ATTGCCTGGAGGGAGGAGGCTGTTTTGTTTGAAGCTT                         5917
```

FIG. 2

```
Size     501 , Select      1
    1 ATGCGCTGTGGACCCCTGTGCCGATTCCTGCTGGCTTTGGCCTATCTGTCCTACGTTGAA    60

1  M  R  C  G  P  L  C  R  F  L  L  A  L  A  Y  L  S  Y  V  E    20

61 GCCGTGCCCATCTGGAGAGTCCAGGATGACACCAAAACCCTCATCAAGACGATTGTCACC   120

21  A  V  P  I  W  R  V  Q  D  D  T  K  T  L  I  K  T  I  V  T    40

121 AGGATCAGTGACATTTCACACATGCAGTCTGTCTCCTCCAAACAGAGGGTCACCGGTTTG   180

41  R  I  S  D  I  S  H  M  Q  S  V  S  S  K  Q  R  V  T  G  L    60

181 GACTTCATCCCTGGGCTCCATCCTGTCCTGAGTTTGTCCAAGATGGACCAGACCCTGGCG   240

61  D  F  I  P  G  L  H  P  V  L  S  L  S  K  M  D  Q  T  L  A    80

241 ATCTACCAACAGATCCTCACCAGTCTGCCTTCCAGAAATGTGATCCAAATATCGAATGAC   300

81  I  Y  Q  Q  I  L  T  S  L  P  S  R  N  V  I  Q  I  S  N  D   100

301 CTGGAGAACCTCCGGGACCTTCTCCACCTGCTGGCCTCCTCCAAGAGCTGCCCCTTGCCC   360

101  L  E  N  L  R  D  L  L  H  L  L  A  S  S  K  S  C  P  L  P   120

361 AGCAGGGCCCTGGAGACCTTGGAGAGCCTGGGCGGCGTCCTGGAAGCCTCCCTCTACTCC   420

121  S  R  A  L  E  T  L  E  S  L  G  G  V  L  E  A  S  L  Y  S   140

421 ACGGAGGTGGTGGCCCTGAGCAGGCTGCAGGGGGCTCTGCAGGACATGCTGCGGCAGCTG   480

141  T  E  V  V  A  L  S  R  L  Q  G  A  L  Q  D  M  L  R  Q  L   160

481 GACCTCAGCCCTGGCTGCTGA                                            501

```
  1 GTGCCCATCTGGAGAGTCCAGGATGACACCAAAACCCTCATCAAGACGATTGTCACCAGG    60
  1   V   P   I   W   R   V   Q   D   D   T   K   T   L   I   K   T   I   V   T   R     20

61 ATCAGTGACATTTCACACATGCAGTCTGTCTCCTCCAAACAGAGGGTCACCGGTTTGGAC   120
 21   I   S   D   I   S   H   M   Q   S   V   S   S   K   Q   R   V   T   G   L   D     40

121 TTCATCCCTGGGCTCCATCCTGTCCTGAGTTTGTCCAAGATGGACCAGACCCTGGCGATC   180
 41   F   I   P   G   L   H   P   V   L   S   L   S   K   M   D   Q   T   L   A   I     60

181 TACCAACAGATCCTCACCAGTCTGCCTTCCAGAAATGTGATCCAAATATCGAATGACCTG   240
 61   Y   Q   Q   I   L   T   S   L   P   S   R   N   V   I   Q   I   S   N   D   L     80

241 GAGAACCTCCGGGACCTTCTCCACCTGCTGGCCTCCTCCAAGAGCTGCCCCTTGCCCAGC   300
 81   E   N   L   R   D   L   L   H   L   L   A   S   S   K   S   C   P   L   P   S    100

301 AGGGCCCTGGAGACCTTGGAGAGCCTGGGCGGCGTCCTGGAAGCCTCCCTCTACTCCACG   360
101   R   A   L   E   T   L   E   S   L   G   G   V   L   E   A   S   L   Y   S   T    120

361 GAGGTGGTGGCCCTGAGCAGGCTGCAGGGGGCTCTGCAGGACATGCTGCGGCACGTGGAC   420
121   E   V   V   A   L   S   R   L   Q   G   A   L   Q   D   M   L   R   H   V   D    140

421 CTCAGCCCTGGCTGC                                                435
141   L   S   P   G   C                                            145
```

FIG. 4

|  |  | 10 | 20 | 30 | 40 | 50 |  |
|---|---|---|---|---|---|---|---|
| PIG | 1 | ATGCGCTGTC | GACCCCTGTC | CCGATTCCTG | CTGGCTTTGG | CC-TATCTGT | 50 |
| HUMAN | 1 | ATGCATTGGG | GAACCCTGTC | GGGATTCTTG | -TGGCTTTGG | CCCTATCTTT | 50 |
| MOUSE | 1 | ATGTGCTGGA | GACCCCTGTC | TCGCTTCCTG | -TGGCTTTGG | TCCTATCTGT | 50 |
|  |  | 60 | 70 | 80 | 90 | 100 |  |
| PIG | 51 | CCTACGTTGC | AGCCGTGCCC | ATCTGACAG | TCCAGGATGA | CACCAAAACC | 100 |
| HUMAN | 51 | TCTATGTCCA | AGCTGTGCCC | ATCCAAAAAG | TCCAAGATGA | CACCAAAACC | 100 |
| MOUSE | 51 | CTTATGTTCA | AGCAGTGCCT | ATCCAGAAAG | TCCAGGATGA | CACCAAAACC | 100 |
|  |  | 110 | 120 | 130 | 140 | 150 |  |
| PIG | 101 | CTCATCAAGA | CGATTGTCAC | CAGGATCAGT | GACATTTCAC | ACATGCAGTC | 150 |
| HUMAN | 101 | CTCATCAAGA | CAATTGTCAC | CAGGATCAAT | GACATTTCAC | ACACGCAGTC | 150 |
| MOUSE | 101 | CTCATCAAGA | CCATTGTCAC | CAGGATCATT | GACATTTCAC | ACACGCAGTC | 150 |
|  |  | 160 | 170 | 180 | 190 | 200 |  |
| PIG | 151 | TGTCTCCTCC | AAACAGAGGG | TCACCGGTTT | GGACTTCATC | CCTGGGCTCC | 200 |
| HUMAN | 151 | AGTCTCCTCC | AAACAGAAAG | TCACCGGTTT | GGACTTCATT | CCTGGGCTCC | 200 |
| MOUSE | 151 | GGTATCCGCC | AAGCAGAGGG | TCACTGGCTT | GGACTTCATT | CCTGGGCTTC | 200 |
|  |  | 210 | 220 | 230 | 240 | 250 |  |
| PIG | 201 | ATCCTGTCCT | GAGTTTGTCC | AAGATGGACC | AGACCCTGGC | GATCTACCAA | 250 |
| HUMAN | 201 | ACCCCATCCT | GACCTTATCC | AAGATGGACC | AGACACTGGC | AGTCTACCAA | 250 |
| MOUSE | 201 | ACCCCATTCT | GAGTTTGTCC | AAGATGGACC | AGACTCTGGC | AGTCTATCAA | 250 |
|  |  | 260 | 270 | 280 | 290 | 300 |  |
| PIG | 251 | CAGATCCTCA | CCAGTCTGCC | TTCCAGAAAT | GTGATCCAAA | TATCGAATGA | 300 |
| HUMAN | 251 | CAGATCCTCA | CCAGTATGCC | TTCCAGAAAC | GTGATCCAAA | TATCCAACGA | 300 |
| MOUSE | 251 | CAGGTCCTCA | CCAGCCTGCC | TTCCAAAAAT | GTGCTGCAGA | TAGCCAATGA | 300 |
|  |  | 310 | 320 | 330 | 340 | 350 |  |
| PIG | 301 | CCTGGAGAAC | CTCCGGGACC | TTCTCCACCT | GCTGGCCTCC | TCCAAGAGCT | 350 |
| HUMAN | 301 | CCTGGAGAAC | CTCCGGGATC | TTCTTCACGT | GCTGGCCTTC | TCTAAGAGCT | 350 |
| MOUSE | 301 | CCTGGAGAAT | CTCCGAGACC | TCCTCCATCT | GCTGGCCTTC | TCCAAGAGCT | 350 |
|  |  | 360 | 370 | 380 | 390 | 400 |  |
| PIG | 351 | GCCCCTTGCC | CAG---CAGG | GCCCTGGAGA | CCTTGGAGAG | CCTGGGCGGC | 400 |
| HUMAN | 351 | GCCACTTGCC | CTGGGCCAGT | GGCCTGGAGA | CCTTGGACAG | CCTGGGGGGT | 400 |
| MOUSE | 351 | GGTCCCTGCC | TCAGACCAGT | GGCCTGCAGA | AGCCAGAGAG | CCTGGATGGC | 400 |
|  |  | 410 | 420 | 430 | 440 | 450 |  |
| PIG | 401 | GTCCTGGAAG | CCTCCCTCTA | CTCCACGGAG | GTGGTGGCCC | TGAGCAGGCT | 450 |
| HUMAN | 401 | GTCCTGGAAG | CTTCAGGCTA | CTCCACAGAG | GTGGTGGCCC | TGAGCAGGCT | 450 |
| MOUSE | 401 | GTCCTGGAAG | CCTCACTCTA | CTCCACAGAG | GTGGTGGCTT | TGAGCAGGCT | 450 |
|  |  | 460 | 470 | 480 | 490 | 500 |  |
| PIG | 451 | GCAGGGGGCT | CTGCAGGACA | TGCTGCGGCA | GCTGGACCTC | AGCCCTGGCT | 500 |
| HUMAN | 451 | GCAGGGGTCT | CTGCAGGACA | TGCTGTGGCA | GCTGGACCTC | AGCCCTGGGT | 500 |
| MOUSE | 451 | GCAGGGCTCT | CTGCAGGACA | TTCTTCAACA | GTTGGATGTT | AGCCCTGAAT | 500 |
|  |  | 510 | 520 | 530 | 540 | 550 |  |
| PIG | 501 | GCTGA..... | .......... | .......... | .......... | .......... | 550 |
| HUMAN | 501 | GCTGA..... | .......... | .......... | .......... | .......... | 550 |
| MOUSE | 501 | GCTGA..... | .......... | .......... | .......... | .......... | 550 |

PORCINE LEPTIN PROTEIN, NUCLEIC ACID SEQUENCES CODING THEREFOR AND USES THEREOF

BACKGROUND OF THE INVENTION

1. Field of the Invention

This invention relates to the regulation of energy intake and metabolism in growing, finishing, lactating or nonlactating, and gestating swine. More specifically, it relates to a specific porcine polypeptide termed leptin which is secreted by adipocytes or other cell types and which influences energy intake and metabolism, fat deposition, and weight gain in swine. In addition, this invention relates to the nucleotide sequences encoding the porcine leptin polypeptide, the antibodies directed against the porcine leptin polypeptide, and methods to determine susceptibility to fat deposition, alter energy intake, and minimize excessive fat deposition in swine.

2. Description of the Background Art

Obesity has been declared a public health hazard by the National Institutes of Health and has prompted the food animal industry to seek methods of limiting fat deposition in food animals. Additionally, the energetic cost of having food animals convert feed energy to fat rather than lean tissue provides considerable incentive to develop technology to facilitate the efficient production of leaner meat products and to accurately match the nutrient content of the diet to the nutrient needs of the animal. To combat these health and production problems, both prophylactic and therapeutic approaches are necessary. For prophylactic purposes, it would be useful to be able to predict and measure the propensity or susceptibility to excessive fat deposition. For therapeutic purposes, it would be of great benefit to improve current methods of minimizing the deposition of feed energy as fat in the adipocyte. Currently, neither of these desired objectives has been achieved completely.

Proteins from genes expressed only (or predominantly) in adipose tissue and for which the level of expression can be related to fat deposition serve as prime targets for approaches directed toward prediction of fat accretion potential and the control of fat deposition. For example, a mammalian adipocyte-specific polypeptide, termed p154, was reported in U.S. Pat. No. 5,268,295 to Serrero, which is incorporated in its entirety herein by reference, as being expressed in high quantities in adipogenic cell lines after cell differentiation and is abundant in the fat pads of normal and genetically obese mice. To date, however, there have been no reports of adipocyte-specific proteins expressed at different levels in fat swine as compared with normal controls.

Leptin, the protein produced by the leptin (ob) gene, is possibly related to fat deposition in swine because research has shown that mutations in genetically (ob/ob) obese mice resulting in excessive fat deposition are associated with altered expression of the leptin gene. Furthermore, at least one restriction fragment length polymorphism (RFLP) has been identified and related to the fat phenotype (Zhang et al., 1994, Nature 371:425). The leptin gene is expressed specifically in the terminally differentiated adipocyte (Maffei et al., 1995, Proc. Natl. Acad. Sci. 92:6957; Leroy et al., 1996, J. Biol. Chem. 271(5):2365). Additionally, leptin is a regulator of feed intake (Pellymounter et al., 1995, Sci. 269:540; Halaas et al., 1995, Sci. 269:543; Campfield et al., 1995, Sci. 269:546).

Although the murine teptin gene has been positionally cloned and a cDNA sequence reported (Nature 371:425), neither the porcine leptin cDNA or genomic sequence is available. Thus, the insights obtained with respect to porcine metabolism is not accessible to porcine systems. Furthermore, the biologically active purified porcine protein (i.e., leptin) has not been obtained.

SUMMARY OF THE INVENTION

The present invention provides gene sequences, peptides, antibodies, and methods of using them which permit the prediction and modulation of fat deposition and regulation of feed intake (i.e. appetite) in the porcine species.

In one aspect, this invention is directed to a porcine adipocyte polypeptide, the porcine leptin protein, substantially free of other porcine proteins, or functional derivatives thereof. The present invention includes a porcine adipocyte polypeptide of at least about 8 amino acids of the amino acid sequence depicted in FIGS. 1A–1D (SEQ ID NO:1), preferably the amino acid sequence depicted in FIG. 2 (SEQ ID NO:2), still more preferably, the amino acid sequence depicted in FIG. 3 (SEQ ID NO:3 and SEQ ID NO:4), or functional derivatives thereof.

The present invention is also directed to a single or double stranded DNA molecule or an RNA molecule consisting essentially of a nucleotide sequence that encodes the above polypeptide or functional derivatives thereof, the DNA or RNA molecule being substantially free of other porcine DNA or RNA sequences. The DNA molecule is preferably a single or double stranded DNA molecule having a nucleotide sequence consisting essentially of at least about 20 nucleotides of the nucleotide sequence depicted in FIGS. 1A–1D (SEQ ID NO:1), preferably, the nucleotide sequence encoding the amino acid sequence depicted in FIG. 2, still more preferably the nucleotide sequence depicted in FIG. 3 (SEQ ID NO:3) or a sequence complementary to the nucleotide sequences depicted in FIGS. 1A–3, (SEQ ID NO:1 and SEQ ID NO: 3) substantially free of other porcine DNA sequences. The RNA molecule is preferably an mRNA sequence encoding the above porcine adipocyte polypeptide, or functional derivatives thereof.

Included in the invention is a DNA molecule as described above which is cDNA or genomic DNA, preferably in the form of an expressible vehicle or plasmid.

The present invention is also directed to hosts transformed or transfected with the above DNA molecules, including a prokaryotic host, preferably a bacterium, a eukaryotic host such as a yeast cell, or a mammalian cell.

The present invention also provides a process for preparing a porcine adipocyte polypeptide or functional derivatives as described above, the process comprising the steps of: (a) culturing a host capable of expressing the polypeptide under culture conditions; (b) expressing the polypeptide; and (c) recovering the polypeptide from the culture.

Also included in the present invention is a method for detecting the presence of a nucleic acid molecule having the sequence of the DNA molecule described above, or a complementary sequence, in a nucleic acid-containing sample, the method comprising: (a) contacting the sample with an oligonucleotide probe complementary to the sequence of interest under hybridizing conditions; and (b) measuring the hybridization of the probe to the nucleic acid molecule, thereby detecting the presence of the nucleic acid molecule. The above method may additionally comprise before step (a): (c) selectively amplifying the number of copies of the nucleic acid sequence.

Another embodiment of this invention is an antibody specific for an epitope of the porcine adipocyte polypeptide, or functional derivatives thereof, either polyclonal or monoclonal. Also intended is a method for detecting the presence or measuring the quantity of the porcine adipocyte polypeptide leptin in a biological sample, comprising contacting the sample with the above antibody and detecting the binding of the antibody to an antigen in the sample, or measuring the quantity of antibody bound.

The present invention includes methods for determining the susceptibility of swine to fat deposition which comprises removing a biological sample from a pig and measuring therein the amount of the polypeptide or mRNA coding therefor, where the amount of the polypeptide or mRNA is related to susceptibility. The present invention also includes methods for determining the susceptibility of a subject to fat deposition which comprises removing a biological sample, extracting the DNA, digesting the DNA with restriction endonucleases, probing the sample with an oligonucleotide probe, separating the resulting fragments by gel electrophoresis, and relating the number of bands (banding pattern) generated by restriction enzyme digestion to fat deposition (i.e., RFLP techniques).

Another method provided herein is for evaluating the efficacy of a drug (or other agent) directed to the regulation of fat deposition and feed intake which comprises contacting the drug being tested with an adipocyte culture in vitro and measuring the amount of the porcine adipocyte polypeptide or mRNA that is produced by the adipocyte, the efficacy of the drug or agent being related to changing the production of the polypeptide or mRNA.

BRIEF DESCRIPTION OF THE DRAWINGS

FIGS. 1A–1D depicts the nucleotide sequence of the porcine leptin gene and the amino acid translation of the porcine leptin coding sequences (SEQ ID NO:1 and SEQ ID NO:2).

FIG. 2 depicts the nucleotide sequence and the amino acid translation of the coding region of the entire porcine leptin cDNA (i.e., signal peptide and secreted protein) (SEQ ID NO:1 and SEQ ID NO:2).

FIG. 3 depicts the nucleotide sequence and the amino acid translation of the porcine leptin cDNA corresponding to the secreted porcine leptin protein (SEQ ID NO:3 and SEQ ID NO:4).

FIG. 4 shows a comparison of the porcine leptin cDNA sequence corresponding to the entire porcine leptin protein (SEQ ID NO:1) with the murine (SEQ ID NO:6) and human (SEQ ID NO:5) sequences.

DETAILED DESCRIPTION OF PREFERRED EMBODIMENTS

Figure 5:
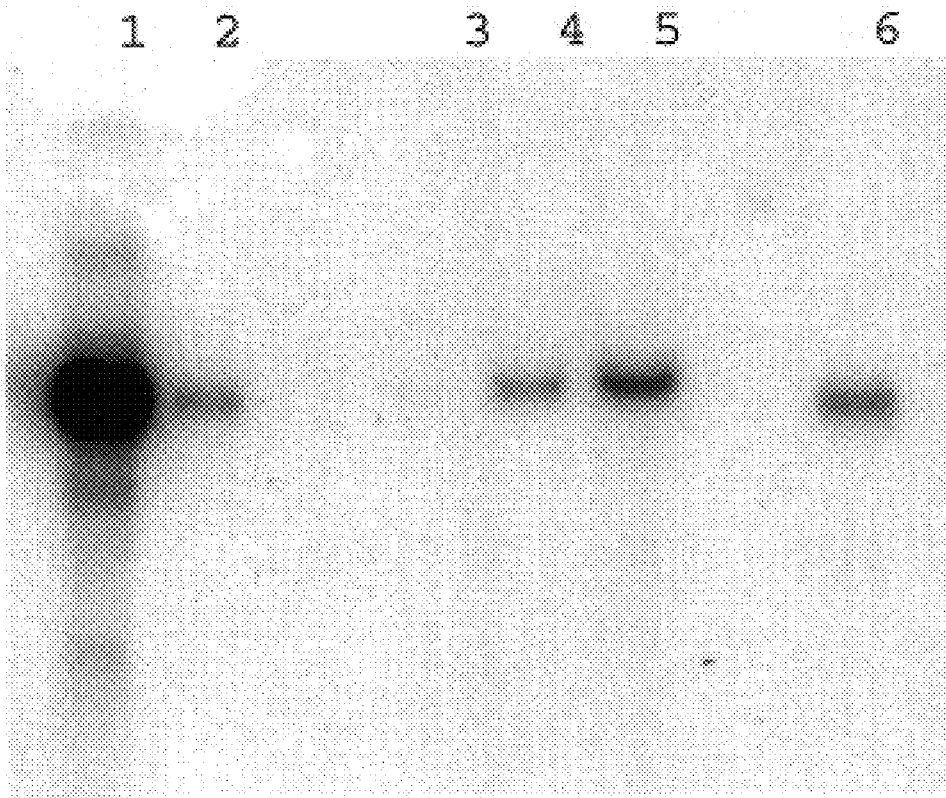
FIG. 5 depicts the Northern blot analysis of porcine leptin mRNA.

The present invention is directed to DNA and RNA molecules that encode a porcine adipocyte polypeptide, termed "leptin," or a functional derivative thereof, and the porcine leptin protein itself, or a functional derivative thereof. The porcine leptin protein is useful for regulation of feed intake, energy metabolism, and fat deposition in swine. Such objectives can be achieved by administering recombinant or purified porcine leptin, altering the expression of the porcine leptin gene or administering an antibody directed against the porcine leptin protein to achieve neutralization, depending on the desired result. The porcine leptin DNA, RNA, and protein, or functional derivatives thereof, and antibodies specific for the protein are used in assays to predict the potential for fat deposition in swine. These molecules can also be utilized in the development of commercially valuable technology for altering feed intake and regulating fat deposition in swine, and for matching the nutrient content of the diet to the nutrient needs of the pig.

In its first aspect, the present invention provides a porcine adipocyte polypeptide termed "leptin". The term "polypeptide" as used herein is intended to include not only the porcine leptin protein, and functional derivatives thereof, but also amino acid sequences having additional components, e.g., amino acid sequences having additional components such as a sugar, as in a glycopeptide, or other modified protein structures known in the art.

The polypeptide of this invention has an amino acid sequence as depicted in FIGS. 1A–1D and 2 (SEQ ID NO:1 and SEQ ID NO:2), and preferably as depicted in FIG. 3 (SEQ ID NO:3 and SEQ ID NO:4). Also intended within the scope of the present invention is any peptide having at least about 8 amino acids present in the above-mentioned sequence. Sequences of this length are useful as antigens and for making immunogenic conjugates with carriers for the production of antibodies specific for various epitopes of the entire protein. Such peptides are also useful in screening such antibodies and in the methods of the present invention directed to detection of the leptin protein in biological samples. It is well-known in the art that peptides of about 8 amino acids are useful in generation of antibodies to larger proteins of biological interest.

The polypeptide of this invention is sufficiently large to comprise an antigenically distinct determinant, or epitope, which can be used as an immunogen to produce antibodies against porcine leptin or a functional derivative thereof, and to test such antibodies. The polypeptide of this invention may also exist covalently or noncovalently bound to another molecule. For example it may be fused (i.e., a fusion protein) to one or more other polypeptides via one or more peptide bonds.

One embodiment includes the polypeptide substantially free of other porcine peptides. The polypeptide of the present invention may be biochemically or immunochemically purified from cells, tissues, or a biological fluid. Alternatively, the polypeptide can be produced by recombinant means in a prokaryotic or eukaryotic host cell.

"Substantially free of other porcine polypeptides" reflects the fact that because the gene for the porcine adipocyte polypeptide of interest can be cloned, the polypeptide can be expressed in a prokaryotic or eukaryotic organism, if desired. Methods are also well known for the synthesis of polypeptides of a desired sequence on solid phase supports and their subsequent separation from the support. Alternatively, the protein can be purified from tissue or fluids of the swine in which it naturally occurs so that it is purified away from at least 90 percent (on a weight basis), and from even at least 99 percent if desired, of other porcine polypeptides and is therefore substantially free of them. That can be achieved by subjecting the tissue or fluids to standard protein purification techniques such as immunoadsorbent columns bearing monoclonal antibodies reactive against the protein. Alternatively, the purification from such tissue or fluids can be achieved by a combination of standard methods, such as ammonium sulfate precipitation, molecular sieve chromatography, and ion exchange chromatography.

As alternatives to a native purified or recombinant porcine adipocyte polypeptide molecule, functional derivatives of the porcine adipocyte polypeptide may be used. As used herein, the term "functional derivative" refers to any "fragment", "variant", "analog", or "chemical derivative" of the porcine adipocyte polypeptide that retains at least a portion of the function of the porcine adipocyte polypeptide which permits its utility in accordance with the present invention.

A "fragment" of the porcine adipocyte polypeptide as used herein refers to any subset of the molecule, that is, a shorter peptide.

A "variant" of the porcine adipocyte polypeptide as used herein refers to a molecule substantially similar to either the entire peptide or a fragment thereof. Variant peptides may be conveniently prepared by direct chemical synthesis of the variant peptide, using methods well-known in the art. Alternatively, amino acid sequence variants of the peptide can be prepared by mutations in the DNA which encodes the synthesized peptide (again using methods well-known in the art). Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structures.

An "analog" of the porcine adipocyte polypeptide as used herein refers to a non-natural molecule substantially similar to either the entire molecule or a fragment thereof.

A "chemical derivative" of the porcine adipocyte polypeptide or peptide as used herein contains additional chemical moieties not normally a part of the polypeptide. Covalent modifications are included within the scope of this invention. Such modifications may be introduced into the molecule by reacting targeted amino acid residues with an organic derivatizing agent that is capable of reacting with selected side chains or terminal residues.

The polypeptide of the present invention is encoded by a nucleic acid molecule, one strand of which has the nucleotide sequence shown in FIGS. 1A–1D (SEQ ID NO:1), preferably the nucleotide sequence enconding the amino acid sequence as shown in FIG. 2 (SEQ ID NO:2), and still more preferably as shown in FIG. 3 (SEQ ID NO:3). The present invention is directed to a DNA sequence encoding the polypeptide, or a functional derivative thereof, substantially free of other porcine DNA sequences. Such DNA may be single stranded (i.e., sense strand, antisense strand or cDNA sequence) or double stranded. The DNA sequence should preferably have about 20 or more nucleotides to allow hybridization to another polynucleotide. In order to achieve higher specificity of hybridization, characterized by the absence of hybridization to sequences other than those encoding the polypeptide or a functional derivative thereof, a length of at least about 50 nucleotides is preferred.

The present invention is also directed to an RNA molecule comprising a mRNA sequence encoding the polypeptide of this invention, or a functional derivative thereof.

The present invention is further directed to the above DNA molecules which are functional in recombinant expression systems utilizing as hosts transfected or transformed with the vehicles and capable of expressing the polypeptide. Such hosts may be prokaryotic or eukaryotic. The DNA can be incorporated into the host organism by transformation, transduction, transfection, or a related process known in the art.

In addition to a DNA and mRNA sequence encoding the porcine adipocyte polypeptide molecule, this invention provides methods for expression of the nucleic acid sequences. Further, the genetic sequences and oligonucleotides of the invention allow the identification and cloning of additional, yet undiscovered adipocyte polypeptides having sequence homology to the adipocyte polypeptide described herein.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al., Prog. Nucl. Acid. Res. Molec. Biol. 21:101–141 (1978), which is incorporated herein by reference. Procedures for constructing recombinant molecules in accordance with the above-described method are disclosed by Sambrook et al. Molecular Cloning: A Laboratory Manual, Second Edition, Cold Spring Harbor Press, Cold Spring Harbor, N.Y. (1989), which is herein incorporated by reference.

Oligonucleotides representing a portion of the porcine adipocyte polypeptide are useful for screening for the presence of genes encoding such proteins and for the cloning of porcine adipocyte polypeptide genes. Techniques for synthesizing such oligonucleotides are disclosed by, for example, Wu, R., et al. Prog. Nucl. Acid. Res. Molec. Biol. 21:101–141 (1978).

A suitable oligonucleotide, or set of oligonucleotides, which is capable of encoding a fragment of the porcine adipocyte polypeptide gene (or which is complementary to such an oligonucleotide, or set of oligonucleotides) is identified, synthesized, and hybridized by means well known in the art, against a DNA or, more preferably, a cDNA preparation derived from cells which are capable of expressing the porcine adipocyte polypeptide gene. Single stranded oligonucleotide molecules complementary to the "most probable" porcine adipocyte polypeptide-encoding sequences can be synthesized using procedures which are well known to those of ordinary skill in the art (See e.g., U.S. Pat. No. 5,268,295). Additionally, DNA synthesis may be achieved through the use of automated synthesizers. Techniques of nucleic acid hybridization are disclosed by Sambrook et al. (supra).

In an alternative way of cloning the porcine adipocyte polypeptide gene, a library of expression vectors is prepared by cloning DNA or, more preferably, cDNA (from a cell capable of expressing the porcine adipocyte polypeptide) into an expression vector. The library is then screened for members capable of expressing a protein which binds to anti-porcine-adipocyte polypeptide antibody, and which has a nucleotide sequence that is capable of encoding polypeptides that have the same amino acid sequence as the porcine adipocyte polypeptide, or fragments thereof. In this embodiment, DNA, or more preferably cDNA, is extracted and purified from a cell which is capable of expressing the porcine adipocyte polypeptide protein. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression vectors of the present invention may be either prokaryotic or eukaryotic. Examples of suitable prokaryotic expression vectors include pASK75 (Biometra) or pET 21a–d (Novagen). Examples of suitable eukaryotic expression vectors include pcDNA3 or pRc/RSV (In Vitrogen, Inc.).

A DNA sequence encoding the porcine adipocyte polypeptide of the present invention, or its functional derivative, may be recombined with vector DNA in accordance with conventional techniques such as those disclosed by Sambrook, et al. (supra).

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression.

The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. A promoter is a double-stranded DNA or RNA molecule which is capable of binding RNA polymerase and promoting the transcription of the "operably linked" nucleic acid sequence. The promoter sequences of the present invention may be either prokaryotic, eukaryotic or viral. Strong promoters are, however, preferred. Suitable promoters are repressible, or more preferably, constitutive. Examples of suitable prokaryotic promoters include the tetracycline (TetA) promoter for pASK75 and T7lac for pET21. Examples of suitable eurkaryotic promoters include alpha actin or beta actin. Examples of suitable viral promoters include Rous sarcoma or cyotmegala.

The present invention is also directed to an antibody specific for an epitope of the porcine adipocyte polypeptide, and the use of such antibody to detect the presence of, or measure the quantity or concentration of the polypeptide, a functional derivative thereof, in a cell, a cell or tissue extract, or a biological fluid. As used herein, the term "epitope" refers to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics. An antibody is said to be "capable of binding" a molecule if it is capable of specifically reacting with the molecule to thereby bind the molecule to the antibody.

The porcine adipocyte polypeptide of the present invention, or a functional derivative thereof, preferably having at least about 8 amino acids is used as an antigen for induction of a polyclonal antibody or monoclonal antibody (mAb). As used herein, an "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The term "antibody" is meant to include polyclonal antibodies, monoclonal antibodies (mAbs), and chimeric antibodies. Polyclonal antibodies are heterogeneous populations of antibody molecules derived from the sera of animals immunized with an antigen. Monoclonal antibodies are a substantially homogeneous population of antibodies to specific antigenic epitopes. MAbs may be obtained by methods known to those skilled in the art. (See, for example Kohler and Milstein, Nature 256:495–497 (1975) and U.S. Pat. No. 4,376,110; de St. Groth, S. F. et al. J. Immunol. Methods, 35:1–21 (1980); and Hartlow, E. et al., Antibodies: A Laboratory Manual, Cold Spring Harbor Laboratory Press, Cold Spring Harbor, N.Y., 1988).

Chimeric antibodies are molecules different portions of which are derived from different animal species, such as those having a variable region derived from a porcine mAb and a murine immunoglobulin constant region. Chimeric antibodies and methods for their production are known in the art (Cabilly et al, Proc. Natl. Acad. Sci. USA 81:3273–3277 (1984); Morrison et al., Pro,. Natl. Acad. Sci. USA 81:6851–6855 (1984); Boulianne et al., Nature 312:643–646 (1984); Neuberger et al., Nature 314:268–270 (1985); Liu et al., Proc. Natl. Acad. Sci. USA 84:3439–3443 (1987); Better et al., Science 240:1041–1043 (1988)). These references are hereby incorporated by reference.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., J. Nucl. Med. 24:316–325 (1983)). Such fragments are typically produced by proteolytic cleavage, using enzymes such as papain (to produce Fab fragments) or pepsin (to produce F(ab')$_2$ fragments).

The reaction of the antibodies and the polypeptides of the present invention are detected by immunoassay methods well known in the art (See, for example, Hartlow et al. supra). The antibodies, or fragments of antibodies, useful in the present invention may be used to quantitatively or qualitatively detect the presence of cells which express the porcine adipocyte polypeptide protein. This can be accomplished by immunofluorescence techniques employing a fluorescently labeled antibody coupled with microscopy, flow cytometric, or fluorimetric detection.

The antibodies (or fragments thereof) useful in the present invention may be employed histologically, as in immunofluorescence or immunoelectron microscopy, for in situ detection of the porcine adipocyte polypeptide. In situ detection may be accomplished by removing a histological specimen from a pig, and providing a labeled antibody of the present invention to such a specimen. The antibody (or fragment) is preferably provided by applying or by overlaying the labeled antibody (or fragment) to a biological sample. Through the use of such a procedure, it is possible to determine not only the presence of the porcine adipocyte polypeptide but also its distribution in the examined tissue. Using the present invention, those of ordinary skill will readily perceive that any of a wide variety of histological methods (such as staining procedures) can be modified in order to achieve such in situ detection.

Such assays for porcine adipocyte polypeptide typically comprise incubating a biological sample, such as a biological fluid, a tissue extract, freshly harvested or cultured cells containing adipogenic cells or adipocytes, in the presence of a detectably labeled antibody capable of identifying the porcine aclipocyte polypeptide, and detecting the antibody by any of a number of techniques well-known in the art, such as enzyme immunoassays (EIA or ELISA) or radioimmunoassays (RIA).

The antibody molecules of the present invention may also be adapted for utilization in an immunometric assay, also known as a "two-site" or "sandwich" assay. In a typical immunometric assay, a quantity of unlabeled antibody (or fragment of antibody) is bound to a solid support (i.e., any support capable of binding antigen or antibodies) and a quantity of detectably labeled soluble antibody is added to permit detection and/or quantitation of the ternary complex formed between solid-phase antibody, antigen, and labeled antibody.

The binding activity of a given lot of antibody to the porcine adipocyte polypeptide may be determined according to well known methods. Those skilled in the art will be able to determine operative and optimal assay conditions for each determination by employing routine experimentation.

Antibodies can be used in an immunoaffinity column to purify the porcine adipocyte polypeptide of the invention by a one step procedure, using methods known in the art.

According to the present invention, a pig that is susceptible to fat deposition is treated with the porcine adipocyte protein to limit such fat deposition. This treatment may be performed in conjunction with other anti-adipogenic therapies. A typical regimen for treating swine with a propensity for fat deposition comprises administration of an effective amount of the porcine adipocyte polypeptide administered over a period of time.

The porcine adipocyte polypeptide of the present invention may be administered by any means that achieve its intended purpose, preferably to alter feed intake or limit fat deposition in a subject. For example, administration may be by various parenteral routes including, but not limited to, subcutaneous, intravenous, intradermal, intramuscular, and intraperitoneal routes. Alternatively, or concurrently, administration may be by the oral route which may be accomplished by the use of genetically-altered feedstuffs, in which the porcine leptin gene has been inserted and expressed. Parenteral administration can be by bolus injection or by gradual perfusion over time such as by implant of osmotic delivery device. Preparations for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

It is understood that the dosage of porcine adipocyte polypeptide administered may be dependent upon the age, sex, health, and weight of the recipient, kind of concurrent treatment, if any, frequency of treatment, and the nature of the effect desired. The most preferred dosage will be tailored to the individual subject, as is understood and determinable by one of skill in the art. The total dose required for each treatment may be administered by multiple doses or in a single dose. The porcine adipocyte polypeptide of the present invention may be administered alone or in conjunction with other therapeutics directed toward the regulation of fat deposition.

In a preferred embodiment, the concentration of the porcine adipocyte polypeptide or mRNA of this invention is measured in a cell preparation, tissue extract or biological fluid of a subject as a means for determining the susceptibility or the propensity of the subject for fat deposition. The susceptibility of the subject to fat deposition is related to the level of the porcine adipocyte polypeptide or its mRNA. Additionally, restriction fragment length polymorphisms in the porcine adipocyte gene will be used to predict fat deposition potential.

Another embodiment of the invention is evaluating the efficacy of a drug or other agent, directed to the increase or decrease of feed intake by measuring the ability of the drug or agent to stimulate or suppress the production of the porcine adipocyte polypeptide, or mRNA of this invention by a cell or cell line capable of producing such polypeptides or mRNAs. Preferred cells are cells of an adipogenic cell line. The antibodies, cDNA probe or riboprobe of the present invention are useful in the method for evaluating these drugs or other agents in that they can be employed to determine the amount of the porcine adipocyte polypeptide or mRNAs using one of the above-mentioned immunoassays.

An additional embodiment of the present invention is directed to assays for measuring the susceptibility of a pig to fat deposition based on measuring in a tissue or fluid from the subject the amount of the mRNA sequences present that encode the porcine adipocyte polypeptide, or a functional derivative thereof, preferably using an RNA-DNA hybridization assay. The susceptibility to fat deposition is related to the amount of such mRNA sequences present. For such assays, the source of the mRNA sequences is preferably a pig's adipogenic cells. The preferred technique for measuring the amount of mRNA is a hybridization assay using RNA (e.g., Ribonuclease Protection Assay) or DNA (e.g. Northern or Slot Blot Assays) of complementary base sequence.

Nucleic acid detection assays, especially hybridization assays, can be predicated on any characteristic of the nucleic acid molecule, such as its size, sequence, susceptibility to digestion by restriction endonucleases, etc. The sensitivity of such assays may be increased by altering the manner in which detection is reported or signaled to the observer. Thus, for example, assay sensitivity can be increased through the use of detectably labeled reagents. A wide variety of such labels have been used for this purpose. Kourilsky et al. (U.S. Pat. No. 4,581,333) describe the use of enzyme labels to increase sensitivity in a detection assay. Radioisotopic labels are disclosed by Falkow et al. (U.S. Pat. No. 4,358,535), and by Berninger (U.S. Pat. No. 4,446,237). Fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. have also been used in an effort to improve the efficiency with which detection can be observed.

One method for overcoming the sensitivity limitation of nucleic acid concentration is to selectively amplify the nucleic acid whose detection is desired prior to performing the assay. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T., et al., etc.

Recently, an in vitro enzymatic method has been described which is capable of increasing the concentration of such desired nucleic acid molecules. This method has been referred to as the "Polymerase Chain Reaction" or "PCR" (Mullis, K. et al., Cold Spring Harbor Symp. Quant. Biol. 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194). The polymerase chain reaction provides a method for selectively increasing the concentration of a particular nucleic acid sequence even when that sequence has not been previously purified anrid is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

Having now generally described the invention, the same will be more readily understood through reference to the following examples which are provided by way of illustration, and are not intended to be limiting of the present invention, unless specified.

EXAMPLE I

ISOLATION OF PORCINE LEPTIN cDNA

The putative secreted portion of porcine leptin gene product was amplified from adipose tissue mRNA using reverse transcriptase-polymerase chain reaction. Four separate cDNA synthesis reactions were carried out using 1–2 µg of porcine adipose tissue total RNA or 1–2 µg of poly A+mRNA, 150 pmol of random hexamer oligonucleotides, 500 nM dNTP, 200 U of MMLV RNase H⁻ reverse transcriptase (Life Technologies, Inc.) in 20 µl of the supplied buffer. The reactions were incubated for 1 h at 37° C. and terminated by heating to 70° C. for 10 min. The leptin cDNA product was amplified by PCR using the following degenerate oligonucleotide primers with restriction site linkers for BamHI/Bsa I and EcoRI/Eco47 III, respectively:

Sense strand:

5'-GGATCCGGTCTCAGGCC GTGCC(C/T)ATCCA(A/G)AAAGTCC-3' (SEQ ID NO:7).

Antisense strand:

5'-GAATTCAGCGCT GCA(C/T)(C/T)CAGGGCT(G/A)A(G/C)(G/A)TC-3' (SEQ ID NO:8)

These oligonucleotide primers were designed from a multiple sequence alignment of the mouse and human cDNA sequences. Approximately 100 ng of adipose tissue cDNA was added as template to 50 µl PCR reactions made in the manufacturers buffer with 100 pmol of each primer and 2.5 U of Taq DNA polyrnerase (Life Technologies, Inc.). A three stage amplification was carried out under the following conditions; Stage 1-95° C., 3 min; 52° C., 1 min, 72° C. 1 min, 1 cycle; Stage 2-94° C., 45s; 52° C., 45s, 72° C., 1 min, 4 cycles; Stage 3-94° C., 45 s; 55° C., 30 s, 72° C. 1 min, 28 cycles. Template cDNA from three out of four cDNA reactions produced a 466 bp product.

The PCR products were prepared for ligation into the protein expression vector pASK75 (Biometra Inc.) by complete digestion with Eco47III and partial digestion with Bsa I. The restriction enzyme digested PCR products were purified by electrophoresis in low melting point agarose and a 437 bp product was excised from the gel and ligated into the vector. The ligations were transformed in *E. coli* XL1-Blue (Stratagene Inc.) and plated on LB plates containing 50 µg/ml ampicillin for plasmid selection. Twelve *E. coli* colonies were isolated that contained the porcine leptin cDNA, and plasmid DNA was isolated for DNA sequencing.

The nucleotide sequence of the porcine leptin gene comprising 5917 base pairs, and the amino acid translation of the leptin coding sequences are depicted in FIGS. 1A–1D (SEQ ID NO:1). The nucleotide sequence and the amino acid sequence of the entire porcine leptin cDNA (i.e., signal peptide and secreted proteins) comprising 501 base pairs and 167 amino acids are depicted in FIG. 2 (SEQ ID NO:1 and SEQ ID NO:2). The nucleotide sequence and the amino acid sequence of the porcine leptin cDNA corresponding to the secreted protein alone and comprising 435 base pairs and 145 amino acids are depicted in FIG. 3 (SEQ ID NO:3 and SEQ ID NO:4).

There was an 83% identity between the pig (SEQ ID NO:1) and human (SEQ ID NO:5) cDNA sequence and a 76% identity between the pig (SEQ ID NO:1) and mouse (SEQ ID NO:6) cDNA sequence as depicted in FIG. 4.

EXAMPLE II

ISOLATION OF mRNA CORRESPONDING TO PORCINE LEPTIN cDNA

The porcine leptin cDNA was used as a probe for detection of the full length mRNA. A northern blot containing porcine adipose and bovine adipose poly A+mRNA as well as ob/ob mouse adipose total RNA was provided by Dr. M. Spurlock of Purina Mills Inc. The blot was hybridized with an [$^{32}$P] dCTP labeled porcine leptin cDNA in hybridization solution (HY; 0.9 M NaCl, 0.09 M sodium citrate, 0.05% ficoll, 0.05% polyvinylpyrolidone, 0.05% BSA, 0.5% SDS, 0.1% sodium pyrophosphate, 10 mM EDTA and 100 mg/ml sonicated salmon sperm DNA at 60° C. for 15 h. The blot was washed to a final stringency of 0.2×SSC (0.03 M NaCl, 0.003 M sodium citrate), 0.1% SDS at 60° C. and exposed to X-ray film. A 3,090 bp leptin mRNA was detected in porcine and bovine adipose tissue and a 3,240 bp leptin mRNA was detected on ob/ob mouse adipose tissue. As shown in FIG. 5, lanes 1 and 2 contain the porcine adipose poly A+mRNA, lane 3 contains the adipose total RNA from a control mouse and lanes 4 and 5 contain the adipose total RNA from an ob/ob mouse, and lane 6 contains the bovine adipose poly A+mRNA.

EXAMPLE III

ISOLATION OF GENOMIC DNA CLONE CORRESPONDING TO PORCINE LEPTIN

The porcine leptin cDNA was also used to screen a porcine genomic DNA library. Specifically, a porcine genomic library containing 4.64×10⁵ recombinants was previously constructed in SuperCos 1 (Stratagene, Inc.) and screened for porcine leptin. Specifically, two sets of replica filters were prehybridized for 2 h at 60° C. Filters were hybridized overnight with [$^{-32}$P] dCTP labeled probe at 5×10⁵ cpm per ml of hybridization solution at 65° C. Filters were sequentially washed in 2×SSC (0.3 M NaCl, 0.03 M sodium citrate), 0.5% SDS; 1×SSC, 0.5% SDS; and 0.2× SSC 0.5% SDS with each wash at 60° C. for 30 min. Positive clones that showed signals on both replica filters were recovered from the agar plates and individual colonies were isolated by a second low density replica plating and hybridization step. A cosmid designated Obg-361 was isolated that hybridized to the porcine ob cDNA probe and had essentially the same restriction enzyme digestion pattern as found in porcine genomic DNA.

Figure 6:
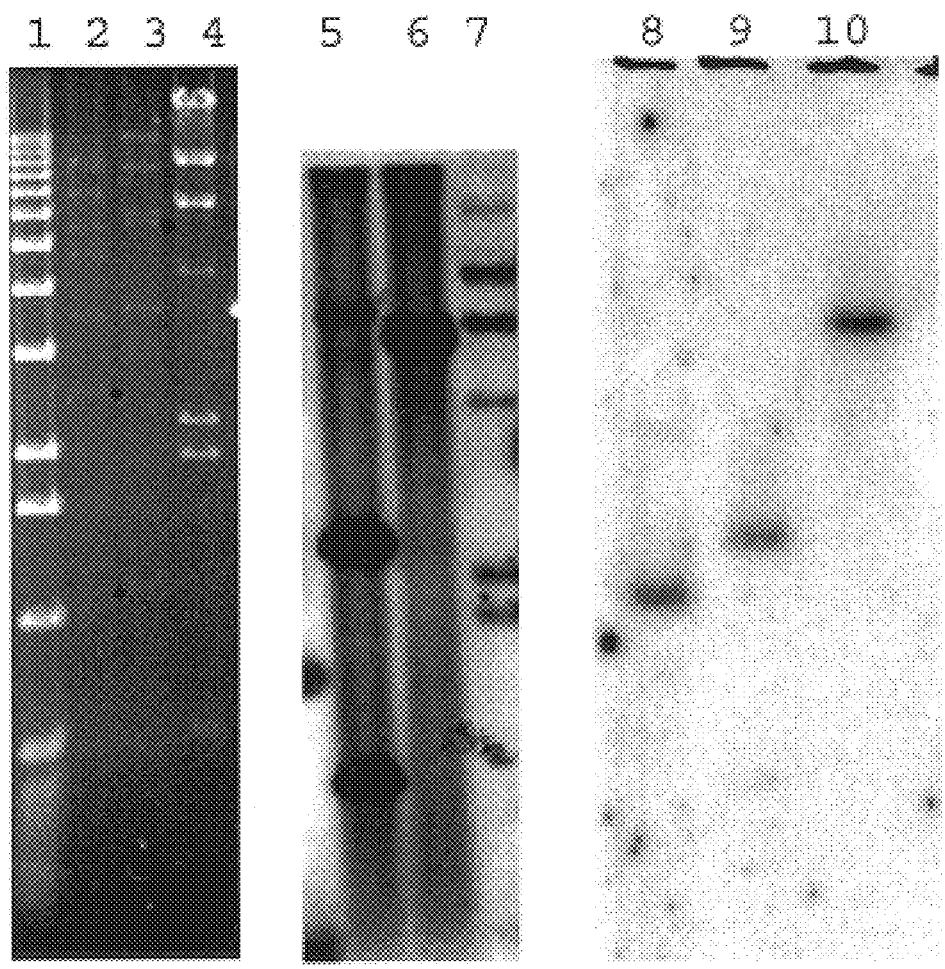
FIG. 6 depicts the isolation of a genomic DNA clone for porcine leptin.

FIG. 6 illustrates the isolation of the cosmid Obg-361. Specifically, lanes 1–4 are an agarose gel containing Kb ladder molecular mass markers (lane 1), cosmid Obg-361 digested with Eco RI (lane 2) and Hind III (lane 3) and biotinylated lambda/Hind III molecular mass markers (lane 4).

Southern blot analysis of the gel in lanes 2–4 were probed with the porcine leptin cDNA indicate that the EcoRI fragments (lane 5) and the Hind III fragments (lane 6) contain leptin sequences. Lane 7 is lambda/Hind III molecular mass markers.

Porcine genomic DNA digested with BAM HI (lane 8), EcoRI (lane 9) and Hind III (lane 10) and hybridized with a Bsa I fragment (300 bp) of the porcine leptin cDNA showed equivalent bands that contain leptin sequences indicating that the porcine leptin gene was isolated in cosmid Obg-361.

The 5917 bp Hind III fragment was subcloned into Bluescript II SK+ (Stratagene, Inc.). Both strands of the sequence was determined using progressive nested deletions using Exonuclease III and Mung Bean nuclease. Sequencing reactions were carried out with Sequenase V2.0. This sequence was 5917 bp in length and contains the entire coding region in two exons (FIGS. 1A–1D (SEQ ID NO:1). There was 78.6% nucleotide identity between the pig and human as well as 71.2% nucleotide identity between pig and mouse coding sequences. The splice junctions for the two exons were confirmed by the cDNA sequence. The cDNA sequence of the protein coding region is shown in FIG. 2 (SEQ ID NO:1 and SEQ ID NO:2). The 501 bp sequences encodes 166 amino acid residue leptin polypeptide with a predicted molecular mass of 18,334 Da.

A clone was obtained using the process described above, Obg H3–15, was deposited with the American Type Culture Collection (ATCC), 12301 Parklawn Drive, Rockville, Md., 20852–1776, on Jul. 11, 1996, and has been designated ATCC No. 97653. This microorganism was deposited under the conditions of the Budapest Treaty on the International Recognition of Deposit of Microorganisms for the purpose of Patent Procedure. All restrictions on the availability to the public of the material so deposited will be irrevocably removed upon the granting of a patent. This deposit will be maintained for a time period of 30 years from the date of deposit or 5 years after the last request for the material, whichever is longer.

EXAMPLE IV

PURIFICATION OF THE PORCINE LEPTIN GENE PRODUCT

The polypeptide sequence encoded by the porcine leptin cDNA was synthesized and purified using the Strep-Tag system (Biometra, Inc.). The pASK plasmid contains the ompA leader sequence for secretion of the protein into the periplasmic space of *E. coli* as well as a ten amino acid carboxyl terminus that brands to strepavidin for affinity chromatography. Synthesis of the porcine leptin protein by *E. coli* strain XL1-Blue was induced with 200 μg/l of anhydrotetracycline and the cells harvested after 3 h. The proteins in the periplasmic space were isolated by osmotic shock by suspending the cells in 100 mM Tris-HCl pH 8.0, 500 mM sucrose, 1 mM EDTA and 0.02% $NaN_3$ for 30 m at 4° C. The cells were removed by centrifugation and the porcine leptin protein was purified from the periplasmic proteins by strepavidin affinity chromatography as depicted in FIG. 5.

Figure 7:
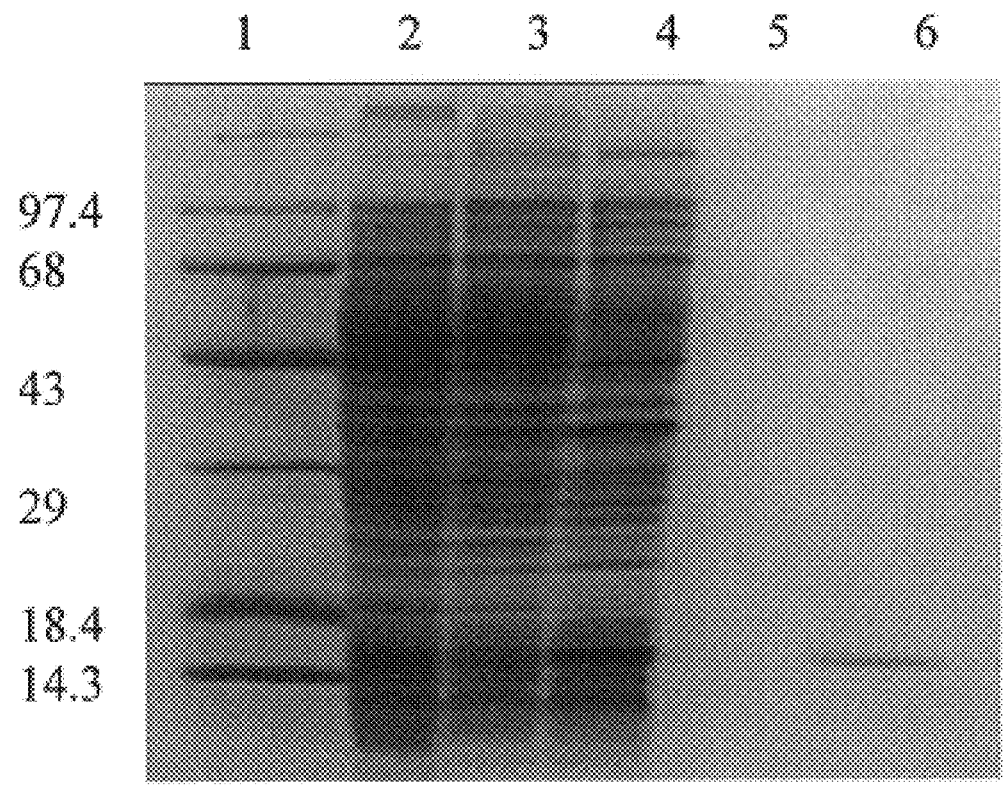
FIG. 7 depicts a polyacrylamide gel electrophoresis of porcine leptin protein induction and purification in *Escherichia coli*.

Specifically, FIG. 7 shows the polyacrylamide gel electrophoresis of porcine leptin protein induction and purification in *E. coli*. Molecular mass markers are located in lane 1. Lane 2 contains total protein from XL-1 Blue and an pASK/Ob cell line before (lane 3) and after (lane 4) anhydrotetracycline induction. Affinity purified porcine leptin protein is located in lane 6.

EXAMPLE V

ANTIBODIES TO PORCINE LEPTIN PROTEIN AND THEIR USE TO DETECT PORCINE LEPTIN IN ADIPOGENIC CELLS

Polyclonal and/or monoclonal antibodies are produced with the recombinant porcine leptin protein. The techniques used for producing, screening, detecting, and/or quantifying antibodies for porcine leptin are discussed extensively in "Antibodies: a Laboratory Manual" (Harlow et al., 1988, Cold Spring Harbor laboratory). All media or medium components, mouse or cell strains (e.g. BALB/C mouse, sp2/0 myeloma cells, JA744A.1 macrophages etc.) are commercially available.

A. Immunization of Animals

1. Rabbits:

Purified porcine leptin protein is injected into rabbits for production of polyclonal antibodies. Specifically, each rabbit receives repeated subcutaneous injections with antigen in Freund's complete adjuvant followed by at least 1 booster injection of about 200 μg to 1 mg. When the serum titer of the immunized rabbits is sufficiently high when tested using the porcine leptin as antigen, rabbit serum is harvested as the polyclonal antiserum for porcine leptin.

2. BALB/C mice (4-week old):

Purified porcine leptin protein is injected into BALB/C mice for production of monoclonal antibodies. Specifically, each mouse is injected with about 50 μg porcine leptin protein with Ribi's S-TDCM adjuvants (RIBI ImmunoChem Research, Inc., Hamilton, Mont.). The number of injections depends on the titer of the antibody in the serum of immunized mice as determined by ELISA using porcine leptin as the antigen. In the course of producing monoclonal antibodies against porcine leptin protein, the spleens of immunized mice are used to prepare spleenocytes. Hybridoma cells are made by fusing the spleenocytes with sp2/0 myeloma cells (treated with 8-Azaguanine containing medium) in the presence of 50% PEG-1500. Hybridoma cells are incubated in selection HAT (hypoxanthine, aminopterine, and thymidine) medium. Subsequent screening for positive clones uses the recombinant porcine leptin as aintigen in ELISA methodology. Positive clones that produce strong anti-porcine-leptin antibody are characterized for specificity, subtype, affinity, binding sites, etc.

When large quantities of purified antibody are needed, the positive clones are cultured in large scale and antibody purified from the culture supernatant, or injected into the intraperitoneal cavity of BALB/C mice for production of ascites. The latter procedure requires about $1-2 \times 10^6$ hybridoma cells per mouse, and usually takes about 7–14 days.

Large quantities of antibody is then purified from ascites by ammonium sulphate precipitation and ion exchange chromatography (e.g. DEAE-Trisacryl M).

Having now fully described this invention, it will be appreciated by those skilled in the art that the same can be performed within a wide range of equivalent parameters, concentrations, and conditions without departing from the spirit and scope of the invention and without undue experimentation. While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 5917 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: join(942..1085, 3400..3753)

(xi) SEQUENCE DESCRIPTION: SEQ ID NO:1:

```
AAGCTTTCTT GGCCCCTAAC AGCAACCACA TTATACTCTT ACTGGCTATT CCTTGGCCTT      60

CAATACCCAG CCCAGGGGAC CCCTCTTCCA GGGAGCCCCG CTTGTACTCC TGAGATGTCA     120

TGTCCTTCTT GCAGAGCTCT TCCTCACGGC ATCGGGACGG CGGTTCACCC TTTTGCCTCT     180

CCGGATAAAC TGTAAGCTAC TTGAGAGCAG AGAACATCCA TTGTTCGCTG TGGCATCCGT     240

GGTACCTAGC ACGGCATCTG ACATATTATC AGATCTTCCA CAAAGGCCAG TTTACGGTTG     300

AATGCCCGTT GAATTCAGGC TCCCAGTGGG AGAGCGAGGA AGTAATAAAG CCGGTGATAA     360

ATGCCGCCGT GGAGACACCA GCGGGCTGCC GTGAGACTAA TGGAGAGGAC AGTAACGTTA     420

TCTCTAATGC GAGGGTGGTT ATAGAGTACA TTTCATAACA CCTTTAAAGC TCTTTCACAC     480

GCATTATCCA ATTTGATCCT CATAAAAGCC TGGAGATGTG TATATTGTGG TGGATGGAGG     540

GGGAGTCTTT AGCAGTTATG GGATATGCCT GAAGTCGTGC AGCTAGTAAA TGGCTGGATT     600

CAAACCAGAC CTCAAAAGCC TGCCTGTTTG CTCATGCCCC CTGCCCCGAC TGCCCACTCT     660

GTGGCCCACA GCACAACTCA CCGTCGCTTT CTTGATCCGT TTTCTTGATC CGGCTGTGCT     720

CTCCCCAAGG AATGCTTTTC ATTAACATAT GTCTAGGTAA TGAATTATCT TGACTCTGAG     780

GAGGCCATAG CACATGCCGT AACGCGACAG CTCCTTTGAT CTGCATCTGA GGCTGTGGCT     840

GGTAACGGGC GTGGGAGGG GGCGTTCGCT GAGACCCCAG GGACACGCCA TGTGTGGTTC     900

CCTCTGTTTC CAGGCCCCAG AAGCACATCC CGGAAAGGAA A ATG CGC TGT GGA        953
                                             Met Arg Cys Gly
                                               1

CCC CTG TGC CGA TTC CTG CTG GCT TTG GCC TAT CTG TCC TAC GTT GAA      1001
Pro Leu Cys Arg Phe Leu Leu Ala Leu Ala Tyr Leu Ser Tyr Val Glu
 5                  10                  15                  20

GCC GTG CCC ATC TGG AGA GTC CAG GAT GAC ACC AAA ACC CTC ATC AAG      1049
Ala Val Pro Ile Trp Arg Val Gln Asp Asp Thr Lys Thr Leu Ile Lys
             25                  30                  35

ACG ATT GTC ACC AGG ATC AGT GAC ATT TCA CAC ATG GTAGGGAAGG           1095
Thr Ile Val Thr Arg Ile Ser Asp Ile Ser His Met
         40                  45

CCTGGGAGAC AAGGTCGAAC CTGTGGCCAG CCCSGGGGGA GGAGGGGTAC CGGACCTCAG    1155

AGGTTGGCGG AGGTGGGAAG GGTCGGCGGT GGCCTTGACG CCTCCCCCAC CCCCCCCAAC    1215

CAGCTGCCTT TGCTCCTCCG CTTCCCTCAC CGCACCCCCC CACGTCCTTA TCCTCCTTCT    1275

TCCCAGACTG GAATCCTGAT GCCCAGGACT AGAGGAAGCC CTAAAGGTCC TGTGTGCCTT    1335

TGCCAGGTGC GCAGACCCCC CAGCATCATC CCCTCTGGCC TCCATCACGT CTCCGGAATG    1395
```

-continued

```
TTCTAATCTG TAGGAATTCT TCCTGGTGAC AGCTGAACTC TGACCCTGCG GACGCCCCTT    1455

ACTGCTAGTC CTGCCCATTG AGCCTTTTTT CCTATACAAC CCTCTACATG TTTGCAAACT    1515

TCTCTCAATG TCCCCAGGGT GTTTTCTCTG GGGTCCGCAG GCCGAGACCT TCAGCCTCTT    1575

CTCAGCTGAG GTCCGTCTTT AGAATTCAGA AGACGAGGTG TGACTCCTCA CCCTGCTGTT    1635

CCCTCTCTGT AAAATCTCAA GCACGTTAAG TCCCTCCGTG TCTGAAACCT TAGTTTCCCT    1695

CATCCAGATA ATGGGACTGT TACTGGGAAG ATGTTACCGG AATCCAGGGT CTTGCCTCAT    1755

GGAGCTCAAG AATGAACTTG GCGAACGCAC AGGGAGCCGA GCAAGCAGAA GTCTTTATTA    1815

CAGGAAGGCA GACAGCTCCC AGCACAGACA CGGGGAGGGA AGAGTCCCCC CGCCCATTGT    1875

TCTACGGAGG TTTTTATCAC TTAAAGACGG GAGTACCAAT GTGGGTCCA GATATCCGTT     1935

CTTCTTCCCA TTGCCCAGTT TACCTATATG GCGCCTTGTC CAGGAGGGAC TCTGTAGAGT    1995

TAGGGGTGCT CCGTAAGTTT TATGGTGCGT CTGCTCTTCT CTGCCCTAGA CTTAGAGTCG    2055

CCACTCTTTC CATTCTTCTG CTCACAGTCA AATGCATAGG TCAGGGGTTA ATTCCCACCT    2115

TCACAGAAAT CAAATGTCCT TTCAATAGTT AATCTTCCAA TAAGCAAGGC CTGCTTGTCT    2175

TGATTAGTTT TTACAAATCT TAAACCATGG CCATTAATCA GGGAAGAGAT CGAAGCCCAT    2235

GTTCCCACAC TAACTGCCTG AATTATTAGT CTGCCTCAGG ACTATCTTAA TAGTCTTCGC    2295

AAGGTTGTTT TGAGATTAAA TTAGATAGGA GTTCCTGTCG AGGCGCGACG GAAACAGATC    2355

CGACTCAGAA CCATGAGACA GGTTCGATCC CTGGCTTTGT CAGTGGGTTA GGATCTGGTG    2415

CTGCTGTGAG CTGTGGTGTA GGTCGCAGAG GTGGCTCGGA TCCCGCGTTG CTGTGGCTGT    2475

GGTGTAGGCC GGTGCAGACA GCTCCGATTA GACCCCTAGC CTGGGAACCT CCATGTGCCG    2535

CGGGTACCGC TAAAAAAAGA CAAAAGATGG AAAAAAAAAA GGTTACATTA GATAAAGCAA    2595

GTGACTCCTC CACCACCACA CATATCCCTG CAGAACCAGG ACAGAGCATG CCTTCTTGAA    2655

AAGTTTTCGG TTGTGGCTTT GATAGCACCC AGCCTTAAAA GCCAGCTTTT CAATCTGCCC    2715

AGAGCAGTCT GGAGACTTCC GCATCTCCTG GCCACTCTGA GTTTCTAACA GTGGCCTTGG    2775

CGAGCCTGGG AGCAGTCCGG TGGCCAGAAG CAGGGACAGC TGAGAACCAG ATAGAGTCTT    2835

GGCACTTTCA AGAGAAAACC CTAAGTCTCC TTCTTCCAGC CATGCAACAG CTGCGCATGA    2895

CAGATCCAGC GTGTCCCAGC CTGTGTGGTG CAGGGAGTGA YGCTGCGNNY AGGGYGYGGG    2955

GGAGCTGAGG AGCGAGGCGG GGCATCGNGG GGCTGCAGCC TCCATCCCTA AGTGGGGAGA    3015

CTTCATGAAG AGCCTGACCA GNAGGGAGGG GCATGTGTGG AGGACCTCAG GGCCTGGGGA    3075

AGGCTAGACC CAACTATGTG AGAAACAGAC AGTCGTGGCT GGTTCTACAG AAGAGGCATC    3135

TGGAGGCCAT TCGAATGCCC AAAGCTGTCT GGGTGAGGCA GGGCTTGCTA GGCAGAAGAC    3195

AGAAGGCCGT GAGACCAGCT TGGAGGCTTG GCAGCCACGC CAGCCCAAGG AGTTCGGGCC    3255

TAGATAGGAT TGTGTGGAAG GGGAAGAGGC AGCCGGAGGT GGGGGGTGGG GGTGGACCCG    3315

TCTCCACGCC TGCAGGAAGG CCAGGGGCTG CAGAGCCAAC ATCTCTCTCG CTGAGCGTCT    3375

CGCTCTCCCC TTCCTCCTGC ACAG CAG TCT GTC TCC TCC AAA CAG AGG GTC      3426
                              Gln Ser Val Ser Ser Lys Gln Arg Val
                                       50              55

ACC GGT TTG GAC TTC ATC CCT GGG CTC CAT CCT GTC CTG AGT TTG TCC     3474
Thr Gly Leu Asp Phe Ile Pro Gly Leu His Pro Val Leu Ser Leu Ser
         60              65              70

AAG ATG GAC CAG ACC CTG GCG ATC TAC CAA CAG ATC CTC ACC AGT CTG     3522
Lys Met Asp Gln Thr Leu Ala Ile Tyr Gln Gln Ile Leu Thr Ser Leu
 75              80              85
```

```
CCT TCC AGA AAT GTG ATC CAA ATA TCG AAT GAC CTG GAG AAC CTC CGG    3570
Pro Ser Arg Asn Val Ile Gln Ile Ser Asn Asp Leu Glu Asn Leu Arg
 90              95                 100                 105

GAC CTT CTC CAC CTG CTG GCC TCC TCC AAG AGC TGC CCC TTG CCC AGC    3618
Asp Leu Leu His Leu Leu Ala Ser Ser Lys Ser Cys Pro Leu Pro Ser
            110                 115                 120

AGG GCC CTG GAG ACC TTG GAG AGC CTG GGC GGC GTC CTG GAA GCC TCC    3666
Arg Ala Leu Glu Thr Leu Glu Ser Leu Gly Gly Val Leu Glu Ala Ser
        125                 130                 135

CTC TAC TCC ACG GAG GTG GTG GCC CTG AGC AGG CTG CAG GGG GCT CTG    3714
Leu Tyr Ser Thr Glu Val Val Ala Leu Ser Arg Leu Gln Gly Ala Leu
            140                 145                 150

CAG GAC ATG CTG CGG CAG CTG GAC CTC AGC CCT GGC TGC TGAAGCTTG      3763
Gln Asp Met Leu Arg Gln Leu Asp Leu Ser Pro Gly Cys
        155                 160                 165

AAGGCCTCTC TCCCCACAGT CGGGGGAAGA AACCTGAGCT TCCAGGAGTC TGCTGGAGAA  3823

GAGAGCCTGT GCGGACCTCC TCTCTGCAGG TCTGCGGACC ATTTCTCTCT CGCTCCGCTA  3883

AGCTGCTCTT CCAAAGGCAG AAAACTCCAA GGCACGACAC CAAAGACAGA AAGGCCTGGT  3943

TCCGCGCCCA CCGGAAAGGG GGCGCCGTCC AGCCAACGGT GGACTAGATT TCGGATTTTC  4003

CACCAACGTC TTCCTTCCTG TTCCATCTCC AGCTCACCGC GTGCTTCAGC GTGACCGGGG  4063

GGATTTCAGA GCCTTTCGAC CATCAAGCAG GGTTCCATCT GAGAATTCCG GGGAGCACGG  4123

TGAAGGCTAC AGGCACACAC AGCTGGATGC TCCCACGCAA CACAAGTTGG AAGCATTTCT  4183

TTATTTATTA TGCGGTGTAT TCTGGTTGGA TTTGAAGCAA ACACCAGCC TTTCCAGGCT   4243

CTCTGGGGTC AGCCGGGGCT AGGGGGAGGC TCCCGAGGTG CTGTTTCCAG TACCATCCAT  4303

GGGCCTGCTG AGGCCAACCC ATTTTGAGTG ACTTGAGGGC TCTCAAGGTC GTTCTCTAGA  4363

GACTGGCTTT GTTTCTACTG TGACTGACTT TAAAACTGCA GCGTGTGCAC TGGCATCGCC  4423

TGCGCGGATC TCGAAGGGCC AGGTTCTCTT AGAAAGAAGA AGATGAACTT TGTCAGGGGT  4483

GTGTACGCGG AGACAGGAAG TGTGTTGGTG GGCGGGGCAT GGATCCAGAA TGTGTATTTC  4543

TTGTGTGATG ACATTTGTG TGAGGGGCTC TCTGGACAGG GTGAGGTCAT TGTCTCATCT   4603

TCGTGGTTTT CATGAGAGAA GGAGATGATT CCTTCACGGG GGTCGTGGGG TTTTGCCAGC  4663

CGCCCGTGCA GGAGTGGGGA AGGGGCTGAA GCCGAAGACC GTTGGGGGCC GTGGTGAGCT  4723

CTGCCTTCTC CAGCTGCTAG AGGCTGGTCT TTCTCATCAG GGAGTGAGGG TCTCGCGTTG  4783

GAGACAGTGA TCCCCAGGGC GGGATCCTTG CCGTGGCCCT CTGAATGGTC TGGGTGATCC  4843

CACACTGATG TCATAACAGG GAAGTGCCCT GGTTTGGGAT TTGTATGCTC ACCCAAAGCA  4903

AGGGCCTGCT TCCCATCCAT TTTGGGAAGG ATTTTTTCTC CAGGGGGAGG GTGAAAGCTC  4963

TGGGAGGTCT GTGGGCTTAC GAGATGGTCC AAGTCCTGGG TCAGTGAGTC CCGGGACTCG  5023

TGACCGCCTC GAGGAGCCCC CTTCTCCCTA CAGGTCATGT TCAATAGGTC AAACAAGGAG  5083

GCATGGGTTT CCACCATCCT GCCGCTGTGA TGCAGCCATC GCACTACAGG AGGTAGATCT  5143

GTCCAAGGAA ATTTGAATCT CAAGCAATCA CTTTCAAGAC TGAGCATCTA TTGTGCTCAG  5203

CCCCAACTGG TGCTATGGGC TCAGAGAAGC TCATCAAATA AATATTAAAA TCCAGTCCTG  5263

CCTTCAGGAC CTTGCATTCC AGATGATAAC ACCTCCCCCA CACCCCGTCT GCAGAGGCTG  5323

TCATTTCACC ATGGCAACCG AGCAGCTGAA ACACAGTGCG GTCCTCAGCA GGTGGAAAGG  5383

CTGAGCTGAG GAGGGCAGTG CCCGGGCCCA CAGGCTAACC CTGCTTGCAC TTGGTAGCAT  5443

TTTTACTGTT CGGGGCGCAT CAGCATCTAT TACTGAGAAG CCGCATCCCT TTGAAGCAGG  5503

ATAGCTGAGA CTATAAAAAT AAGAAAATAC CAGAGTTCCC TTGTGGCACA GAGGGCTAAG  5563
```

```
GATCCAGTGT TGTTGCTGCA GCAGCTTGGG TCACGGCTGT GGCAAGGGTT CGATCCCTGG      5623

CCTGGGAACT TTCACATGTT GCAGGCAAGG CCAAAAAAAA ATAAATAAAT AAAAATAAAC      5683

AAAAAAAAAC AAGACCATAA CAGCAGACTG GTGGCAAACC AGGACTAGAA CCTGGGTCCT      5743

CTGACCCCTA GAGTCAGTGT CCCCTGAGCC AGCTAGTGTT CTCTGGGGAC GGGAACAGGG      5803

TTGGGCAGGG AGTTCAGGAA GTGTTTGCTG GAAGAGCGGA GTTTCCAGGC TGATTTTGCA      5863

GGAGGTGAGG GAAGTGGATT GCCTGGAGGG AGGAGGCTGT TTTGTTTGAA GCTT            5917
```

(2) INFORMATION FOR SEQ ID NO:2:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Cys Gly Pro Leu Cys Arg Phe Leu Leu Ala Leu Ala Tyr Leu
  1               5                  10                  15

Ser Tyr Val Glu Ala Val Pro Ile Trp Arg Val Gln Asp Asp Thr Lys
             20                  25                  30

Thr Leu Ile Lys Thr Ile Val Thr Arg Ile Ser Asp Ile Ser His Met
         35                  40                  45

Gln Ser Val Ser Ser Lys Gln Arg Val Thr Gly Leu Asp Phe Ile Pro
     50                  55                  60

Gly Leu His Pro Val Leu Ser Leu Ser Lys Met Asp Gln Thr Leu Ala
 65                  70                  75                  80

Ile Tyr Gln Gln Ile Leu Thr Ser Leu Pro Ser Arg Asn Val Ile Gln
                 85                  90                  95

Ile Ser Asn Asp Leu Glu Asn Leu Arg Asp Leu Leu His Leu Leu Ala
            100                 105                 110

Ser Ser Lys Ser Cys Pro Leu Pro Ser Arg Ala Leu Glu Thr Leu Glu
        115                 120                 125

Ser Leu Gly Gly Val Leu Glu Ala Ser Leu Tyr Ser Thr Glu Val Val
    130                 135                 140

Ala Leu Ser Arg Leu Gln Gly Ala Leu Gln Asp Met Leu Arg Gln Leu
145                 150                 155                 160

Asp Leu Ser Pro Gly Cys
                165
```

(2) INFORMATION FOR SEQ ID NO:3:

(i) SEQUENCE CHARACTERISTICS:
        (A) LENGTH: 435 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..435

(xi) SEQUENCE DESCRIPTION: SEQ ID NO:3:

```
GTG CCC ATC TGG AGA GTC CAG GAT GAC ACC AAA ACC CTC ATC AAG ACG        48
Val Pro Ile Trp Arg Val Gln Asp Asp Thr Lys Thr Leu Ile Lys Thr
  1               5                  10                  15
```

-continued

```
ATT GTC ACC AGG ATC AGT GAC ATT TCA CAC ATG CAG TCT GTC TCC TCC        96
Ile Val Thr Arg Ile Ser Asp Ile Ser His Met Gln Ser Val Ser Ser
            20                  25                  30

AAA CAG AGG GTC ACC GGT TTG GAC TTC ATC CCT GGG CTC CAT CCT GTC       144
Lys Gln Arg Val Thr Gly Leu Asp Phe Ile Pro Gly Leu His Pro Val
                35                  40                  45

CTG AGT TTG TCC AAG ATG GAC CAG ACC CTG GCG ATC TAC CAA CAG ATC       192
Leu Ser Leu Ser Lys Met Asp Gln Thr Leu Ala Ile Tyr Gln Gln Ile
        50                  55                  60

CTC ACC AGT CTG CCT TCC AGA AAT GTG ATC CAA ATA TCG AAT GAC CTG       240
Leu Thr Ser Leu Pro Ser Arg Asn Val Ile Gln Ile Ser Asn Asp Leu
 65                 70                  75                  80

GAG AAC CTC CGG GAC CTT CTC CAC CTG CTG GCC TCC TCC AAG AGC TGC       288
Glu Asn Leu Arg Asp Leu Leu His Leu Leu Ala Ser Ser Lys Ser Cys
                    85                  90                  95

CCC TTG CCC AGC AGG GCC CTG GAG ACC TTG GAG AGC CTG GGC GGC GTC       336
Pro Leu Pro Ser Arg Ala Leu Glu Thr Leu Glu Ser Leu Gly Gly Val
                100                 105                 110

CTG GAA GCC TCC CTC TAC TCC ACG GAG GTG GTG GCC CTG AGC AGG CTG       384
Leu Glu Ala Ser Leu Tyr Ser Thr Glu Val Val Ala Leu Ser Arg Leu
            115                 120                 125

CAG GGG GCT CTG CAG GAC ATG CTG CGG CAC GTG GAC CTC AGC CCT GGC       432
Gln Gly Ala Leu Gln Asp Met Leu Arg His Val Asp Leu Ser Pro Gly
        130                 135                 140

TGC                                                                    435
Cys
145

(2) INFORMATION FOR SEQ ID NO:4:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:4:

Val Pro Ile Trp Arg Val Gln Asp Asp Thr Lys Thr Leu Ile Lys Thr
 1               5                  10                  15

Ile Val Thr Arg Ile Ser Asp Ile Ser His Met Gln Ser Val Ser Ser
            20                  25                  30

Lys Gln Arg Val Thr Gly Leu Asp Phe Ile Pro Gly Leu His Pro Val
        35                  40                  45

Leu Ser Leu Ser Lys Met Asp Gln Thr Leu Ala Ile Tyr Gln Gln Ile
 50                  55                  60

Leu Thr Ser Leu Pro Ser Arg Asn Val Ile Gln Ile Ser Asn Asp Leu
 65                 70                  75                  80

Glu Asn Leu Arg Asp Leu Leu His Leu Leu Ala Ser Ser Lys Ser Cys
                85                  90                  95

Pro Leu Pro Ser Arg Ala Leu Glu Thr Leu Glu Ser Leu Gly Gly Val
            100                 105                 110

Leu Glu Ala Ser Leu Tyr Ser Thr Glu Val Val Ala Leu Ser Arg Leu
        115                 120                 125

Gln Gly Ala Leu Gln Asp Met Leu Arg His Val Asp Leu Ser Pro Gly
    130                 135                 140

Cys
145
```

(2) INFORMATION FOR SEQ ID NO:5:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
ATGCATTGGG GAACCCTGTG CGGATTCTTG TGGCTTTGGC CCTATCTTTT CTATGTCCAA      60
GCTGTGCCCA TCCAAAAAGT CCAAGATGAC ACCAAAACCC TCATCAAGAC AATTGTCACC     120
AGGATCAATG ACATTTCACA CACGCAGTCA GTCTCCTCCA AACAGAAAGT CACCGGTTTG     180
GACTTCATTC CTGGGCTCCA CCCCATCCTG ACCTTATCCA AGATGGACCA GACACTGGCA     240
GTCTACCAAC AGATCCTCAC CAGTATGCCT TCCAGAAACG TGATCCAAAT ATCCAACGAC     300
CTGGAGAACC TCCGGGATCT TCTTCACGTG CTGGCCTTCT CTAAGAGCTG CCACTTGCCC     360
TGGGCCAGTG GCCTGGAGAC CTTGGACAGC CTGGGGGGTG TCCTGGAAGC TTCAGGCTAC     420
TCCACAGAGG TGGTGGCCCT GAGCAGGCTG CAGGGGTCTC TGCAGGACAT GCTGTGGCAG     480
CTGGACCTCA GCCCTGGGTG CTGA                                           504
```

(2) INFORMATION FOR SEQ ID NO:6:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
ATGTGCTGGA GACCCCTGTG TCGGTTCCTG TGGCTTTGGT CCTATCTGTC TTATGTTCAA      60
GCAGTGCCTA TCCAGAAAGT CCAGGATGAC ACCAAAACCC TCATCAAGAC CATTGTCACC     120
AGGATCAATG ACATTTCACA CACGCAGTCG GTATCCGCCA AGCAGAGGGT CACTGGCTTG     180
GACTTCATTC CTGGGCTTCA CCCCATTCTG AGTTTGTCCA AGATGGACCA GACTCTGGCA     240
GTCTATCCAC AGGTCCTCAC CAGCCTGCCT TCCCAAAATG TGCTGCAGAT AGCCAATGAC     300
CTGGAGAATC TCCGAGACCT CCTCCATCTG CTGGCCTTCT CCAAGAGCTG CTCCCTGCCT     360
CAGACCAGTG GCCTGCAGAA GCCAGAGAGC CTGGATGGCG TCCTGGAAGC CTCACTCTAC     420
TCCACAGAGG TGGTGGCTTT GAGCAGGCTG CAGGGCTCTC TGCAGGACAT TCTTCAACAG     480
TTGGATGTTA GCCCTGAATG CTGA                                           504
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:7:

```
GGATCCGGTC TCAGGCCGTG CCYATCCARA AAGTCC                               36
```

-continued (2) INFORMATION FOR SEQ ID NO:8:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Primer"

(xi) SEQUENCE DESCRIPTION: SEQ ID NO:8:

GAATTCAGCG CTGCAYYCAG GGCTRASRTC        30

What is claimed is:

1. An isolated single or double-stranded DNA molecule consisting of a nucleotide sequence which encodes a porcine adipocyte polypeptide leptin having the amino acid sequence of SEQ ID NO:4, or the complement to the DNA molecule.

2. An expression vector comprising the DNA molecule of claim 1.

3. The vector of claim 2 in which the vector is a plasmid.

4. A host cell transformed or transfected with the plasmid of claim 3.

5. A host cell transformed or transfected with the vector of claim 2.

6. The DNA molecule of claim 1 consisting of the nucleotide sequence of SEQ ID NO:3.

7. An expression vector comprising the DNA molecule of claim 6.

8. The vector of claim 7 in which the vector is a plasmid.

9. A host cell transformed or transfected with the plasmid of claim 8.

10. A host cell transformed or transfected with the vector of claim 7.

11. An isolated mRNA molecule encoding a porcine adipocyte polypeptide leptin, the mRNA molecule encoded by the nucleotide sequence of SEQ ID NO:3.

12. An isolated mRNA molecule consisting of a nucleotide sequence that encodes a porcine adipocyte polypeptide leptin having the amino acid sequence of SEQ ID NO:4.

* * * * *

UNITED STATES PATENT AND TRADEMARK OFFICE
CERTIFICATE OF CORRECTION

PATENT NO.    : 6,277,592 B1
DATED         : August 21, 2001
INVENTOR(S)   : Christopher A. Bidwell and Michael E. Spurlock It is certified that error appears in the above-identified patent and that said Letters Patent is hereby corrected as shown below:

Column 5,
Line 43, replace "enconding" with -- encoding --.

Column 9,
Line 3, replace "aclipocyte" with -- adipocyte --.

Column 11,
Line 7, replace "anrid" with -- and --.

Column 13,
Line 50, replace "brands" with -- binds --.

Signed and Sealed this

Twenty-sixth Day of February, 2002

Attest:

Attesting Officer

JAMES E. ROGAN
Director of the United States Patent and Trademark Office